United States Patent
Ichihashi

(10) Patent No.: US 12,145,000 B2
(45) Date of Patent: Nov. 19, 2024

(54) RADIOTHERAPY SUPPORT SYSTEM AND METHOD

(71) Applicant: Canon Medical Systems Corporation, Otawara (JP)

(72) Inventor: Masahide Ichihashi, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 123 days.

(21) Appl. No.: 17/443,687

(22) Filed: Jul. 27, 2021

(65) Prior Publication Data

US 2022/0023663 A1    Jan. 27, 2022

(30) Foreign Application Priority Data

Jul. 27, 2020 (JP) .................................. 2020-126481
Jul. 26, 2021 (JP) .................................. 2021-121265

(51) Int. Cl.
*A61N 5/10* (2006.01)

(52) U.S. Cl.
CPC .......... *A61N 5/1007* (2013.01); *A61N 5/1031* (2013.01); *A61N 5/1064* (2013.01); *A61N 2005/1098* (2013.01)

(58) Field of Classification Search
CPC .. A61N 5/1007; A61N 5/1031; A61N 5/1039; A61N 5/1064; A61N 2005/1098; A61B 17/3403; A61B 2017/3413
See application file for complete search history.

(56) References Cited

U.S. PATENT DOCUMENTS

| 5,943,719 A * | 8/1999 | Feldman ................ A61B 90/36 |
| | | 606/130 |
| 10,881,375 B2 | 1/2021 | Takimoto et al. |
| 2003/0147495 A1* | 8/2003 | Kato ...................... A61N 5/103 |
| | | 378/65 |
| 2006/0039533 A1* | 2/2006 | Weil ....................... A61N 5/103 |
| | | 378/65 |
| 2006/0229551 A1 | 10/2006 | Martinez et al. |
| 2008/0183072 A1 | 7/2008 | Robertson et al. |
| 2010/0130858 A1 | 5/2010 | Arai et al. |
| 2010/0298255 A1 | 11/2010 | Ballesteros et al. |

(Continued)

FOREIGN PATENT DOCUMENTS

| CN | 107970527 A | 5/2018 |
| CN | 109011221 A | 12/2018 |

(Continued)

OTHER PUBLICATIONS

Extended European Search Report issued Jan. 11, 2022 in corresponding European Patent Application No. 21187780.8, 7 pages.

(Continued)

*Primary Examiner* — Carrie R Dorna
(74) *Attorney, Agent, or Firm* — Oblon, McClelland, Maier & Neustadt, L.L.P.

(57) ABSTRACT

A radiotherapy system according to an embodiment obtains a distribution of a medicament administered to a tumor, obtains a distribution of a radiation dose administered to the tumor, and produces a radiotherapy plan for the tumor with a combined use of the medicament and the radiation dose based on the medicament distribution and the dose distribution.

14 Claims, 16 Drawing Sheets

(56) References Cited

U.S. PATENT DOCUMENTS

2012/0259268 A1* 10/2012 Gerrans ............... A61K 9/1647
                                                                                 604/20
2013/0261371 A1* 10/2013 Jaffray ................ A61M 31/005
                                                                                 600/2

FOREIGN PATENT DOCUMENTS

| EP | 1825881 | * | 8/2007 | ............ A61N 5/103 |
|----|---------|---|--------|------------------------|
| JP | 2004-298476 A | | 10/2004 | |
| JP | 2008-515548 A | | 5/2008 | |
| JP | 2012-148117 A | | 8/2012 | |
| JP | 2012-527627 A | | 11/2012 | |
| JP | 5348889 B2 | | 8/2013 | |
| JP | 5416900 B2 | | 11/2013 | |
| JP | 2019-528134 A | | 10/2019 | |
| WO | WO 2011/137514 A1 | | 11/2011 | |
| WO | WO 2012/088535 A1 | | 6/2012 | |
| WO | WO 2018/036854 A1 | | 3/2018 | |

OTHER PUBLICATIONS

Combined Chinese Office Action and Search Report issued Jan. 6, 2024 in Chinese Patent Application No. 202110848498.7, 7 pages.
Office Action issued Apr. 19, 2024, in corresponding European Patent Application No. 21 187 780.8, 5 pages.

\* cited by examiner

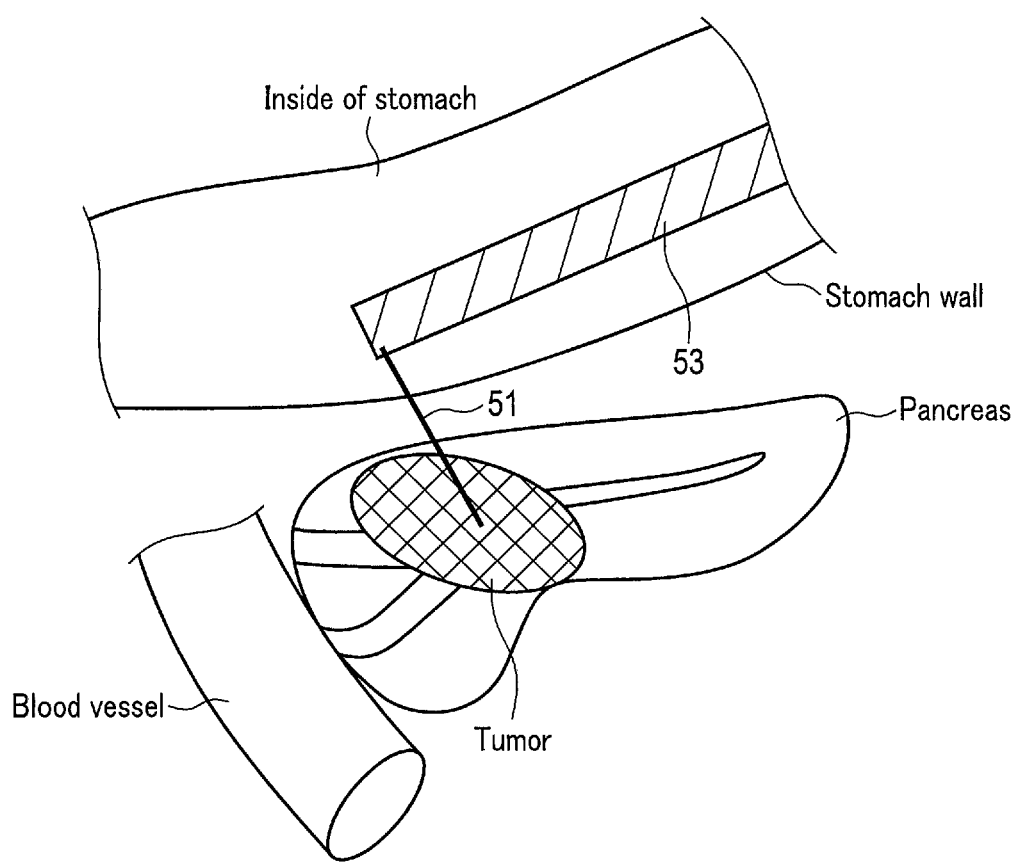
F I G. 3

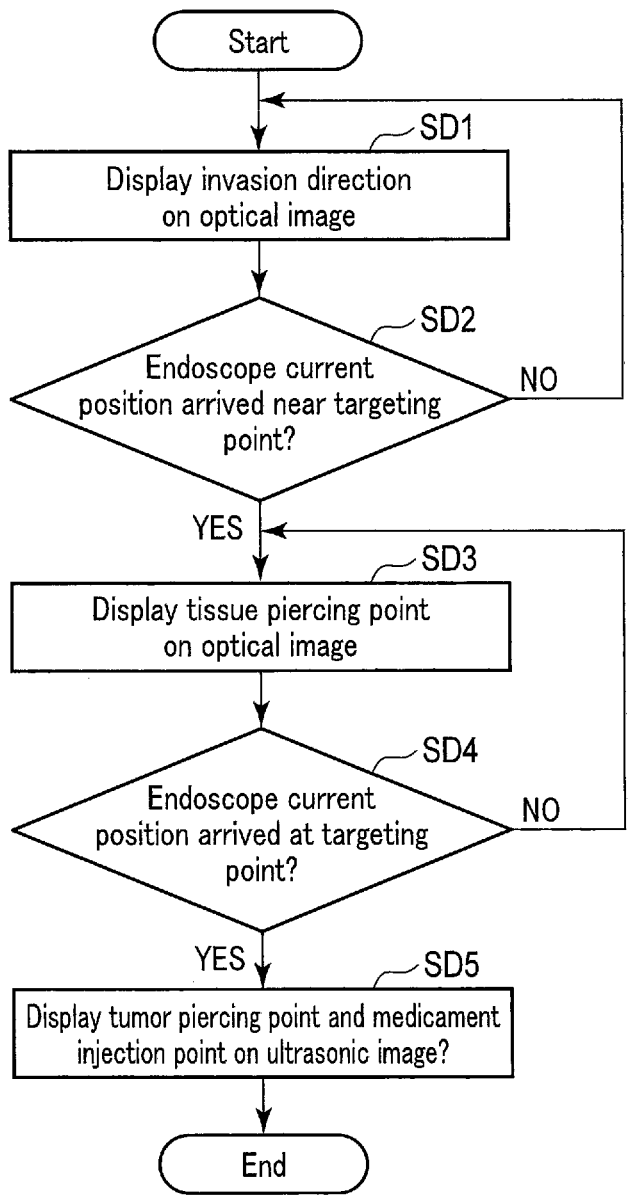
F I G. 15

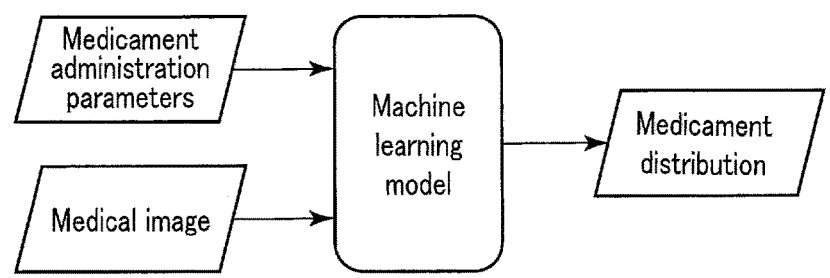
F I G. 19
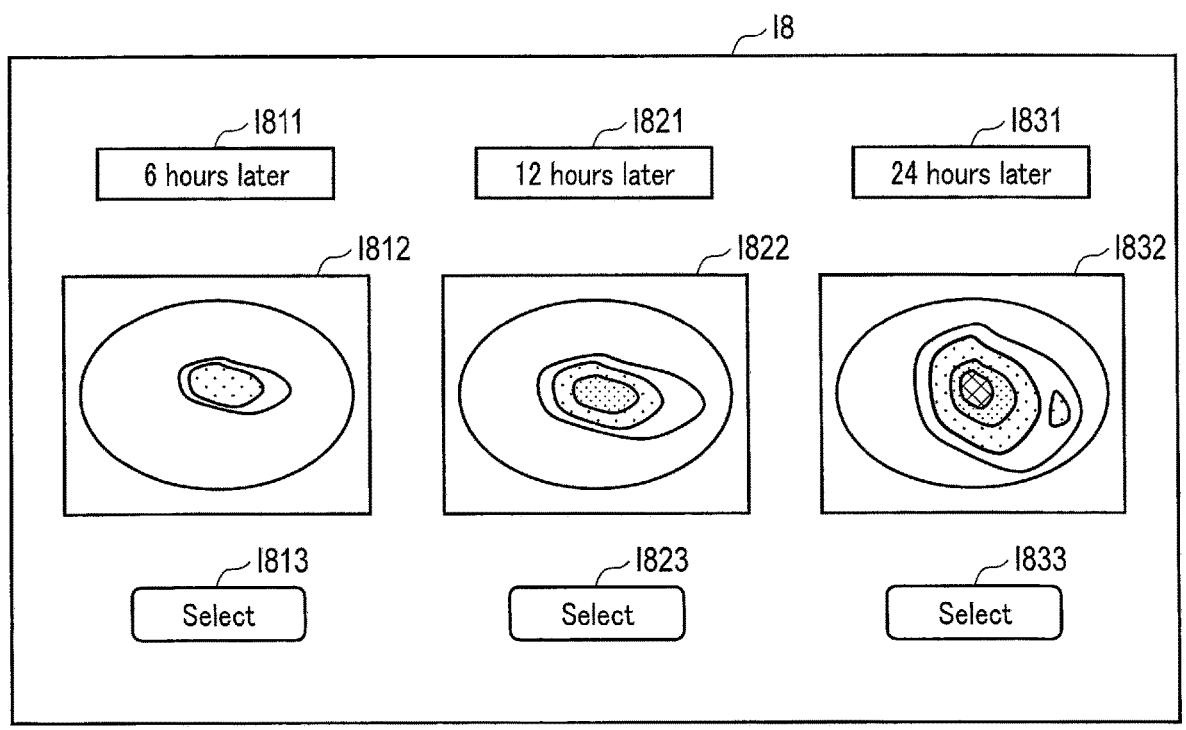
F I G. 20

RADIOTHERAPY SUPPORT SYSTEM AND METHOD

CROSS-REFERENCE TO RELATED APPLICATIONS

This application is based upon and claims the benefit of priority from Japanese Patent Application No. 2020-126481, filed Jul. 27, 2020; and No. 2021-121265, filed Jul. 26, 2021; the entire contents of all of which are incorporated herein by reference.

FIELD

Embodiments described herein relate generally to a radiotherapy support system and method.

BACKGROUND

To improve therapeutic effects of radiotherapy, etc., methods are known such as a method of injecting a medicament such as a radiosensitizer or a carcinostatic, etc. into a tumor or the vicinity thereof under guidance of ultrasound or an endoscope and a method of injecting a medicament containing antibody that specifically accumulates in a tumor. These medicament injections have been performed in a trial-and-error manner based on knowledge and experience of a technician.

BRIEF DESCRIPTION OF THE DRAWINGS

FIG. 3 is a diagram schematically showing an example of a medicament administration technique using an ultrasonic endoscope.

FIG. 15 is a diagram showing a flow of a medicament administration guiding process by the medicament guiding apparatus.

FIG. 19 is a diagram showing an input/output relationship of a machine learning model that generates medicament distribution.

FIG. 20 is a diagram showing an example of a designation window for radiation timing.

DETAILED DESCRIPTION

A radiotherapy system according to an embodiment obtains a distribution of a medicament administered to a tumor, obtains a distribution of a radiation dose applied to the tumor, and produces a radiotherapy plan for the tumor with a combined use of the medicament and the radiation dose based on the medicament distribution and the dose distribution.

Hereinafter, embodiments of a radiotherapy support system and method will be explained in detail with reference to the accompanying drawings.

A radiotherapy support system according to an embodiment is a computer system that supports radiotherapy in conjunction with a use of a medicament administered to a tumor of a patient. To that end, the radiotherapy support system according to the present embodiment supports injection of a medicament using a medicament injection device for administering the medicament to a patient's tumor. Known medicament administration techniques are intra-body injection methods with which an endoscope having a puncture needle is inserted into the body and a medicament is injected through the puncture needle placed inside the body, and under-skin injection methods with which a needle is inserted from the skin and a medicament is injected under the skin. The radiotherapy support system according to the embodiment is compatible with any type of injection method; to make the descriptions hereinafter specific, assume that the system is compatible with intra-body injection methods. Puncture is an act of inserting a needle into a blood vessel, bone marrow, or a cavity of synovial joints, or an abdominal cavity to collect a specimen, such as blood, cerebrospinal fluid, synovial fluid, or ascites. Injection is a method of administrating medicine by inserting a needle into the skin, muscles, or a vessel, etc. to deliver a liquid into the body.

A medicament administered to a tumor may be, for example, a medicament such as a radiosensitizer or a carcinostatic, or a medicament containing an antibody that specifically accumulates on a tumor. By using these medicaments in conjunction with radiation, potentiation in reducing of a tumor size can be expected in radiotherapy.

Figure 1:
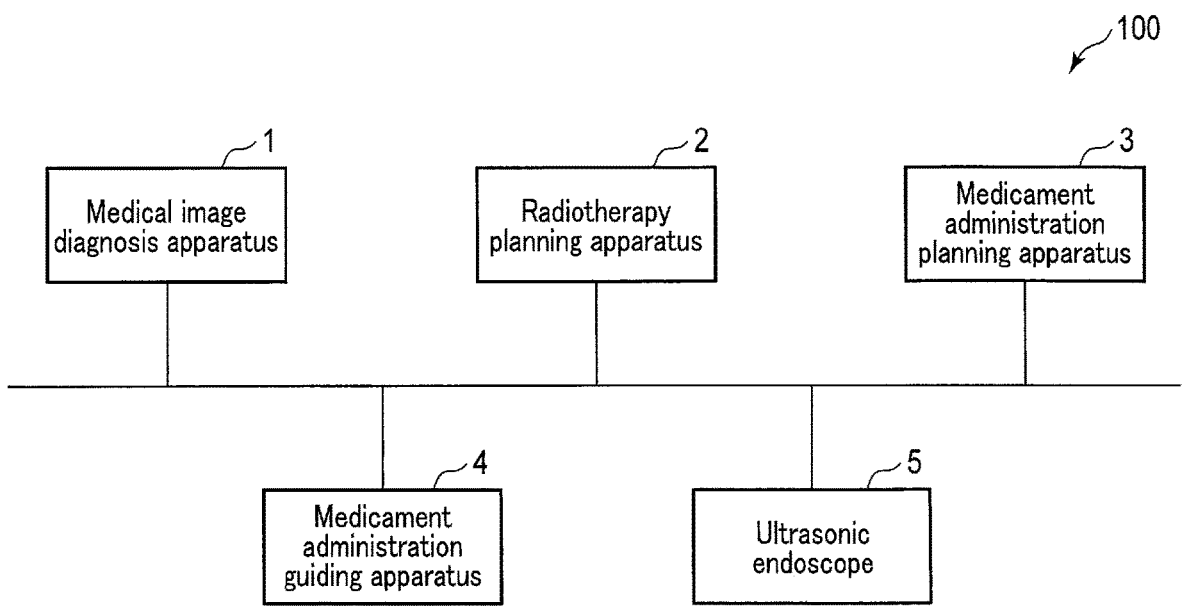
FIG. 1 is a diagram showing a configuration of a radiotherapy support system.

FIG. 1 is a diagram showing a configuration of a radiotherapy support system 100. As shown in FIG. 1, the radiotherapy support system 100 has a medical image diagnosis apparatus 1, a radiotherapy planning apparatus 2, a medicament administration planning apparatus 3, a medicament administration guiding apparatus 4, and an ultrasonic endoscope 5.

The medical image diagnosis apparatus 1 performs medical imaging on a patient who is a target for medicine administration in order to generate a medical image of the patient. The medical image diagnosis apparatus 1 may have any type of imaging principle, as long as it is capable of generating a medical image in which forms and/or properties of anatomical tissue inside a patient's body are shown; for example, an X-ray image diagnosis apparatus, an X-ray computed tomography apparatus, a magnetic resonance imaging apparatus, an ultrasonic image diagnosis apparatus, or a nuclear medicine diagnostic apparatus may be used. In the embodiment, an X-ray computed tomography apparatus or a magnetic resonance imaging apparatus is suitable, as they excel in showing forms of anatomical tissue and can be used for radiotherapy planning.

The X-ray computed tomography apparatus radiates X-rays from an X-ray tube while rotating a rotating frame holding the X-ray tube and an X-ray detector at high speed, and detects the X-rays transmitted through a patient using the X-ray detector. The X-ray computed tomography apparatus then generates a CT image expressing the spatial distribution of X-ray attenuation coefficients of substances present inside of a patient's body, based on raw data from the X-ray detector. In a magnetic resonance imaging apparatus, for example, an application of a gradient magnetic field using a gradient magnetic field coil and an application of RF pulses using a transmitter coil are repeated under an application of a static magnetic field using a static field magnet. MR signals whose release from a patient is caused by the RF pulse application are released. The magnetic resonance imaging apparatus receives the released MR signals via a receiver coil and then generates an MR image expressing spatial distribution of the hydrogen atomic nuclei present in the patient's body, based on the received MR signals. A CT image and an MR image are examples of a medical image. A medical image may be a two-dimensional image including a plurality of two-dimensionally arranged pixels, or a three-dimensional image including a plurality of three-dimensionally arranged pixels (voxels).

The radiotherapy planning apparatus 2 is a computer that includes, for example, a processor such as a central processing unit (CPU), a memory such as a read-only memory (ROM) or a random access memory (RAM), a communication interface, a display device, an input interface, and a memory apparatus. The radiotherapy planning apparatus 2 produces a radiotherapy plan for the patient using medical images generated by the medical image diagnosis apparatus 1. There are two types of radiotherapy planning, namely a forward planning method and an inverse planning method. As a radiotherapy plan, the radiotherapy planning apparatus 2 determines radiotherapy conditions, such as the number of radiation gates, a radiation angle, radiation intensity, a collimator opening, and a wedge filter, etc., and determines predicted spatial distribution of an administered dose to a tumor (referred to as "dose distribution" hereinafter) based on the radiotherapy conditions. Radiotherapy conditions and dose distribution are included in a radiotherapy plan.

The medicament administration planning apparatus 3 is a computer that produces a medicament administration plan for the patient, using medical images generated by the medical image diagnosis apparatus 1. The medicament administration plan includes information that supports medicament injection administered for a tumor of the patient. Specifically, the medicament administration plan includes information relating to a targeted position in the patient's body for a medicament injection device, such as the ultrasonic endoscope 5.

The medicament administration guiding apparatus 4 is a computer that guides medicament administration using the ultrasonic endoscope 5, which is a medicament injection device, based on the medicament administration plan produced by the medicament administration planning apparatus 3.

The ultrasonic endoscope 5 is an endoscope having an insertion unit inserted into a patient's luminal tissue, such as an esophagus or a stomach. The endoscope is equipped with an optical imaging apparatus and ultrasonic imaging apparatus at the insertion unit. The optical imaging apparatus generates an optical image of the inside of a patient's luminal tissue, and the ultrasonic imaging apparatus generates an ultrasonic image of the inside of a patient's luminal organ. The ultrasonic imaging apparatus is applicable to any type scanning method, such as a convex method or a radial method. The distal end of the insertion unit is provided with a puncture needle capable of injecting a medicament. The ultrasonic endoscope 5 is an example of a medicament injection device and an imaging unit.

Figure 2:
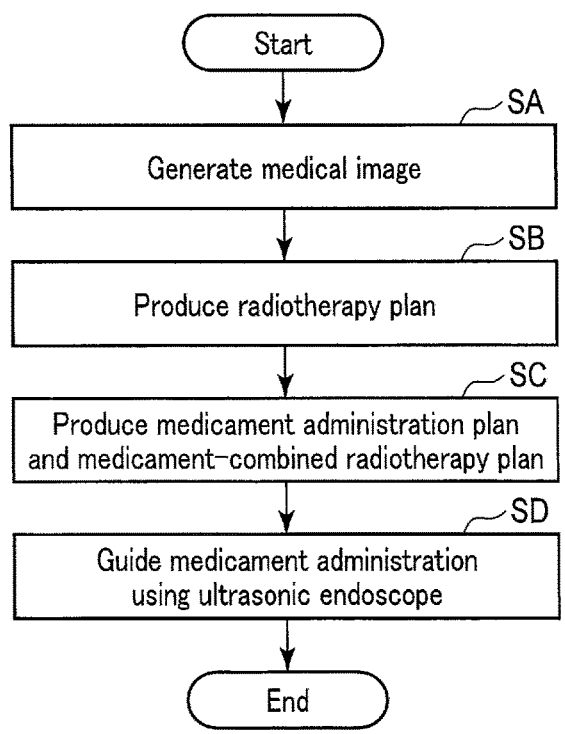
FIG. 2 is a diagram showing an example of a flow of a process in the radiotherapy support system.

FIG. 2 is a diagram showing an example of a flow of a process in the radiotherapy support system 100. As shown in FIG. 2, the medical image diagnosis apparatus 1 performs medical imaging on a patient targeted for medicament administration in order to generate a medical image of the patient (step SA). After step SA is performed, the radiotherapy planning apparatus 2 produces a radiotherapy plan for the patient using the medical image generated in step SA (step SB). After step SB is performed, the medicament administration planning apparatus 3 produces a medicament administration plan and a medication-combined radiotherapy plan for the patient using the medical image generated in step SA (step SC). After step SC is performed, a medicament is administered to the patient using the ultrasonic endoscope 5 before the radiotherapy apparatus begins radiotherapy. At this time, the medicament administration guiding apparatus 4 guides the administration that involves a use of the ultrasonic endoscope 5, based on the medicament administration plan produced in step SC (step SD). Through the guidance based on the medicament administration plan, a technician is able to administer a medicament safely and effectively. When preparation for radiotherapy is completed upon medicament administration, radiotherapy is performed by the radiotherapy apparatus based on the medication-combined radiotherapy plan.

FIG. 3 is a diagram schematically showing an example of a medicament administration technique using the ultrasonic endoscope 5. In the example shown in FIG. 3, the pancreas bears a tumor. As shown in FIG. 3, the pancreas is located close to the stomach, which is a luminal organ. For this reason, when a medicament is administered to the pancreas, it is possible to insert the puncture needle 51 into the pancreas from the inside of the stomach. In more detail, the technician inserts the insertion unit 53 from the mouth and advances it into the stomach. Although not shown, an optical imaging apparatus and an ultrasonic imaging apparatus are provided in the insertion unit 53. The optical image generated by the optical imaging apparatus and the ultrasonic image generated by the ultrasonic imaging apparatus are displayed on the display device in a real-time manner. Together with the optical image and the ultrasonic image, the medicament administration plan is also displayed on the display device. Looking closely at the medicament administration plan, the optical image, and the ultrasonic image, the technician advances the distal end of the insertion unit 53 into the targeted position in the stomach. When the distal end reaches the targeted position, the technician extends the puncture needle 51 provided at the distal end of the insertion unit 53 and inserts the needle into the tumor, and when the tip of the puncture needle 51 reaches the targeted position, the technician then injects the medicament. The medicament injection is thus finished.

The flow of the process shown in FIG. 2 is merely an example, and the flow can be modified in various ways, without being limited to this example. For example, a radiotherapy plan may be produced after a medicament administration plan is produced, and a medicament combined-use radiotherapy plan may be produced thereafter. The radiotherapy support system 100 according to the embodiment is not limited to the use for medicament administration for radiotherapy; it is also applicable to medicament administration for other treatments. In this case, since radiotherapy is not required, there is no need to produce a radiotherapy plan.

Next, the medicament administration planning apparatus 3 used in step SC shown in FIG. 2 is described.

Figure 4:
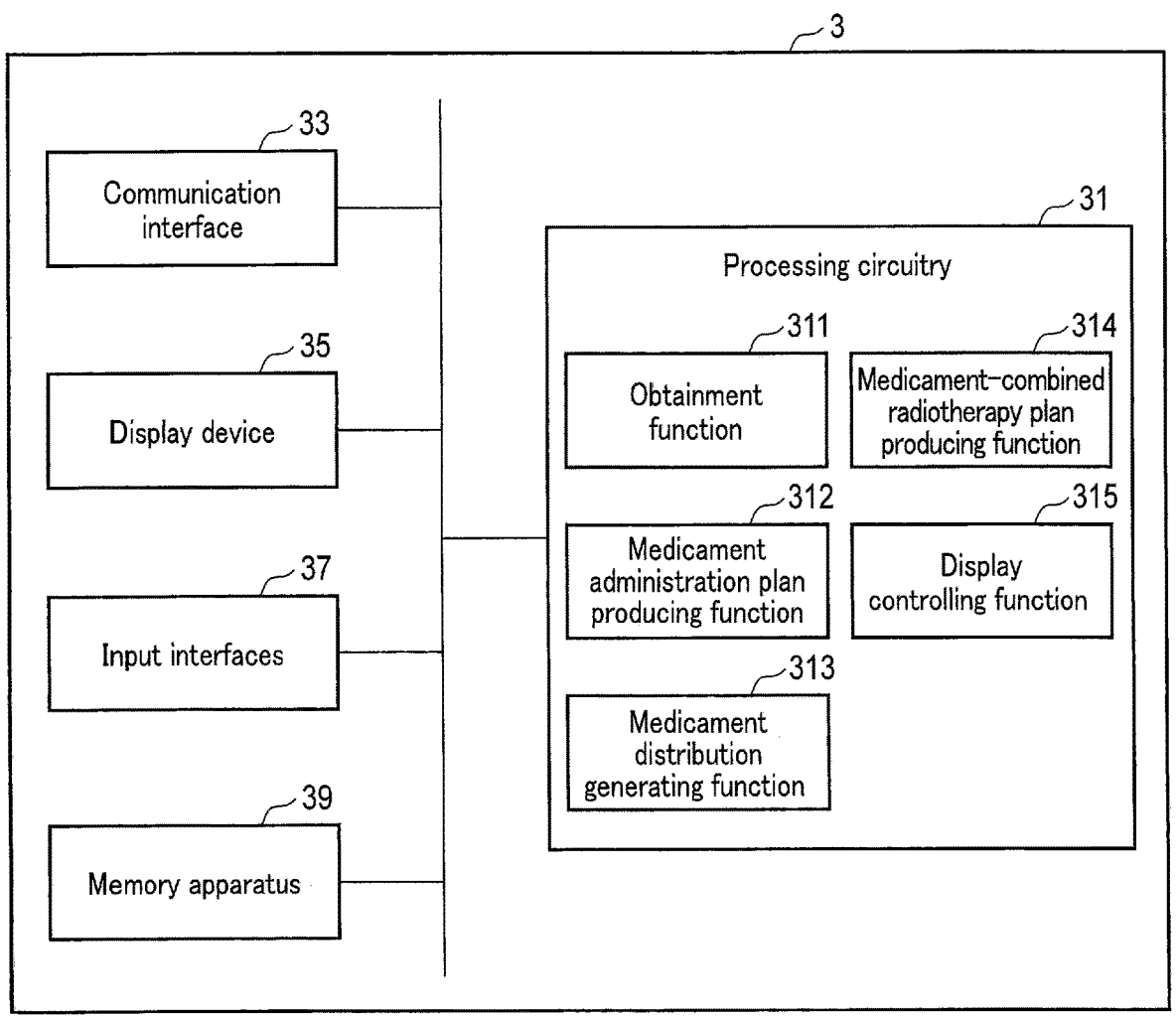
FIG. 4 is a diagram showing an exemplary configuration of a medicament administration planning apparatus.

FIG. 4 is a diagram showing an exemplary configuration of the medicament administration planning apparatus 3. As shown in FIG. 4, the medicament administration planning apparatus 3 includes processing circuitry 31, a communication interface 33, a display device 35, an input interface 37, and a memory apparatus 39. The processing circuitry 31 is an example of a processing unit; the communication interface 33 is an example of a communication unit; the display device 35 is an example of the display unit; the input interface 37 is an example of an input unit; and the memory apparatus 39 is an example of a memory unit.

The processing circuitry 31 has a processor. The processor activates various programs installed on the memory apparatus 39, etc. and thereby realizes an obtainment function 311, a medicament administration plan producing function 312, a medicament distribution generating function 313, a medication-combined radiotherapy plan producing function 314, and a display controlling function 315. Note that the embodiment is not limited to the case in which the respective functions 311 to 315 are realized by single processing circuitry 31. Processing circuitry may be composed by combining a plurality of independent processors, and the respective processors may execute programs, thereby realizing the functions 311 to 315. The obtainment function 311 is an example of an obtainment unit; the medicament administration plan producing function 312 is an example of a producing unit; the medicament distribution generating function 313 is an example of a distribution generating unit; the medication-combined radiotherapy plan producing function 314 is an example of a treatment plan producing unit; and a display controlling function 315 is an example of a display unit.

Through the realization of the obtainment function 311, the processing circuitry 31 obtains various information items. Specifically, the processing circuitry 31 obtains a medical image generated by the medical image diagnosis apparatus 1 and a radiotherapy plan produced by the radiotherapy planning apparatus 2, and the like. A form of the acquisition is not limited to direct acquisition from each apparatus; information received from an apparatus may be stored in the memory apparatus 39 and the information may then be obtained from the memory apparatus 39.

Through the realization of the medicament administration plan producing function 312, the processing circuitry 31 produces a medicament administration plan including a location of a tumor and a targeted position for the ultrasonic endoscope 5 that injects a medicament administered to the tumor, in accordance with forms and properties of a tumor and anatomical tissue shown in the medical image obtained through the obtainment function 311. The targeted position includes at least one of the following: a targeted position for the distal end of the insertion unit of the ultrasonic endoscope 5 (hereinafter, an "endoscope-targeting arrival point"); a targeted position for the puncture needle of the ultrasonic endoscope 5 in a tumor (hereinafter, a "medicament injection point"); a point at which the puncture needle is inserted into a tumor (hereinafter, a "tumor piercing point"); or a location at which the puncture needle is inserted into luminal tissue, such as a stomach (hereinafter, a "tissue piercing point"). The medicament administration plan includes not only a location of a tumor and a targeted position for the ultrasonic endoscope 5 but also parameters related to medicament administration, such as an amount of a medicament to be injected, injection speed, and injection timing, etc.

Through the realization of the medicament distribution generating function 313, the processing circuitry 31 generates a predicted spatial distribution of an amount of administered medicament for a tumor (hereinafter, a "medicament distribution") based on the medical image obtained by the obtainment function 311, an injection point of the medicament, and an injection amount of the medicament. In other words, the processing circuitry 31 generates a medicament distribution based on the medical image and the medicament administration parameters of the medicament administration plan. Each pixel of the medicament distribution is allocated an amount of administered medicament.

Through realization of the medication-combined radiotherapy plan producing function 314, the processing circuitry 31 produces a medication-combined radiotherapy plan, which is a radiotherapy plan for a tumor with a combined use of a medicament and radiation, based on the medicament distribution and dose distribution of radiation. The medication-combined radiotherapy plan includes dose distribution, which is a predicted spatial distribution of radiation administered to a patient in radiation radiotherapy using a combination of a medicament and radiation. The dose distribution of the medication-combined radiotherapy plan is a dose distribution with or without corrections to the dose distribution of the radiotherapy plan. Hereinafter, the dose distribution of the medication-combined radiotherapy plan will be called a "confirmed dose distribution". The dose distribution generated by the radiotherapy planning apparatus 2, etc. will be called an "initial dose distribution". The radiotherapy plan produced by the radiotherapy planning apparatus 2 will be called an "initial radiotherapy plan". For example, the processing circuitry 31 generates a confirmed dose distribution by increasing or decreasing the dose distribution allocated to each pixel of the initial dose distribution.

Through realization of the display controlling function 315, the processing circuitry 31 displays various information items via the display device 35. For example, the processing circuitry 31 displays a medicament administration plan, a medication-combined radiotherapy plan, medicament distribution, initial radiation dose distribution, confirmed dose distribution, and the like.

The communication interface 33 is an interface for information communication among the medical image diagnosis apparatus 1, the radiotherapy planning apparatus 2, the medicament administration guiding apparatus 4, and the ultrasonic endoscope 5 included in the radiotherapy support system 100, via wires or wirelessly.

The display device 35 displays various types of information through the display controlling function 315 of the processing circuitry 31. For the display device 35, a liquid crystal display (LCD), a cathode ray tube (CRT) display, an organic electroluminescent display (OELD), a plasma display, or any other display can be used as appropriate. The display device 35 may be a projector.

The input interface 37 accepts various kinds of input operations from a user, converts the accepted input operations to electric signals, and outputs the electric signals to the processing circuitry 31. Specifically, as the input interface 37, a mouse, a keyboard, a trackball, a switch, a button, a joystick, a touchpad, a touch panel display, etc. can be used as appropriate. The input interface 37 may be an audio input apparatus using audio signals from an input device that collects sound, such as a microphone. The input interface 37 may be a noncontact input circuit using an optical sensor. The input interface 37 outputs electrical signals to the processing circuitry 31 according to an input operation. The input interface 37 may be an input device provided in an external computer connected to the system via a network, etc.

The memory apparatus 39 is a memory apparatus such as a ROM, a RAM, an HDD, an SSD, or an integrated circuit storage unit, etc., configured to store various kinds of information. The memory apparatus 39 stores, for example, medical images and radiotherapy plans, etc. obtained by the obtainment function 311. The memory apparatus 39 may be not only the above-listed memory apparatuses, but also a driver that writes and reads various types of information to and from, for example, a portable storage medium (such as a compact disc (CD), a digital versatile disc (DVD), and a flash memory), or a semiconductor memory. The memory apparatus 39 may be provided in an external computer connected to the medicament administration planning apparatus 3 via wires or wirelessly.

Next, a medicament administration plan producing process by the medicament administration planning apparatus 3 is described. Various embodiment examples can be adopted in the medicament administration plan producing process in accordance with how a medicament administration plan is produced, for example a first embodiment example in which medicament distribution is not used and a second embodiment example in which medicament distribution is used. The embodiment examples are described one by one in the following.

Figure 5:
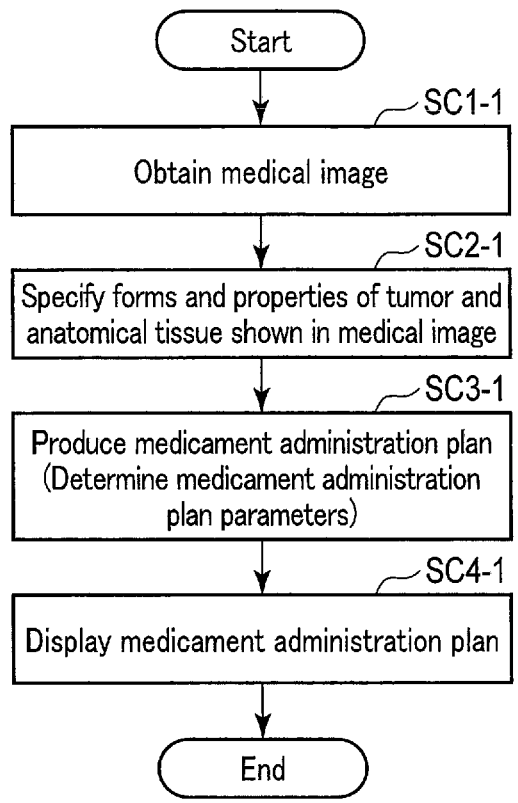
FIG. 5 is a diagram showing a flow of a first embodiment of a medicament administration plan producing process by a medicament administration planning apparatus.

FIG. 5 is a diagram showing a flow of a first embodiment example of a medicament administration plan producing process by the medicament administration planning apparatus 3. As shown in FIG. 5, the processing circuitry 31 obtains a medical image through the realization of the obtainment function 311 (step SC1-1). In step SC1-1, the processing circuitry 31 obtains a medical image of the patient from the medical image diagnosis apparatus 1 via the communication interface 33, for example. As a medical image, a CT image or an MR image is suitable as they excel at showing a patient's anatomical structure. In the following descriptions, the obtained medical image is a three-dimensional image.

After step SC1-1, the processing circuitry 31, through the realization of the medicament administration plan producing function 312, specifies forms and properties of a tumor and anatomical tissue shown in the medical image obtained in step SC1-1 (step SC2-1). In step SC2-1, the processing circuitry 31 performs image recognition on the medical image and performs classification of tumor tissue and anatomical tissue. Tumor tissue is a target of medicament administration, and a single or multiple tumors may be targeted. Anatomical tissue is any kind of human tissue shown in a medical image. It suffices that image recognition is performed through threshold processing or machine learning, for example. Classification of a tumor and anatomical tissue may be performed manually by a user through the input interface 37, etc. Through the classification process, forms of a tumor and anatomical tissue can be specified. These "forms" are information including a location, a shape, and a range of a tumor and anatomical tissue. Specifically, a shape of a tumor, a thickness and a running direction of a blood vessel, and the like.

After forms are specified, the processing circuitry 31 specifies properties of each tumor and piece of anatomical tissue. These "properties" include, for example, a tissue name or a symbol of a site where a tumor occurs, and a tissue name or a symbol of anatomical tissue, and properties exhibited when the tumor or anatomical tissue is subjected to a medicament and/or puncture. The properties exhibited in response to a medicament and/or puncture include information relating to hardness, viscosity, and contraindication. The tissue name or symbol of anatomical tissue can be specified by using anatomical reference points (anatomical landmarks) and machine learning, etc. based on forms of the anatomical tissue. The properties exhibited by anatomical tissue in response to a medicament and/or puncture can be specified by using a lookup table (LUT). For example, a LUT in which the tissue name or symbol of anatomical tissue is associated with information regarding the properties exhibited by the anatomical tissue in response to a medicament and/or puncture (hereinafter, a "property table") is generated in advance, and the processing circuitry 31 inputs the tissue name or symbol of each anatomical tissue item to the table to output properties of the anatomical tissue exhibited for a medicament and/or puncture. A neural network may be used instead of this property table. If pixel values of the medical image are a numerical form of the functions of tissue, these pixel values may be used as properties of the tissue. For example, pixel values of a nuclear medical image represent metabolism of tissue; and pixel values of an ultrasonic Doppler image represent a rate and a direction, etc. of a blood flow; and pixel values of an analysis image based on a contrast CT image or a contrast MR image represent a rate and a flow, etc. of a contrast agent (or a blood flow).

After step SC2-1, the processing circuitry 31, through the realization of the medicament administration plan producing function 312, produces a medicament administration plan (step SC3-1). In step SC3-1, the processing circuitry 31 produces a medicament administration plan image by adding the medicament administration plan parameters, such as a tumor location and targeted positions for the ultrasonic endoscope 5, to the medical image generated in step SC1-1. The generated medicament administration plan is stored in the memory apparatus 39.

Figure 6:
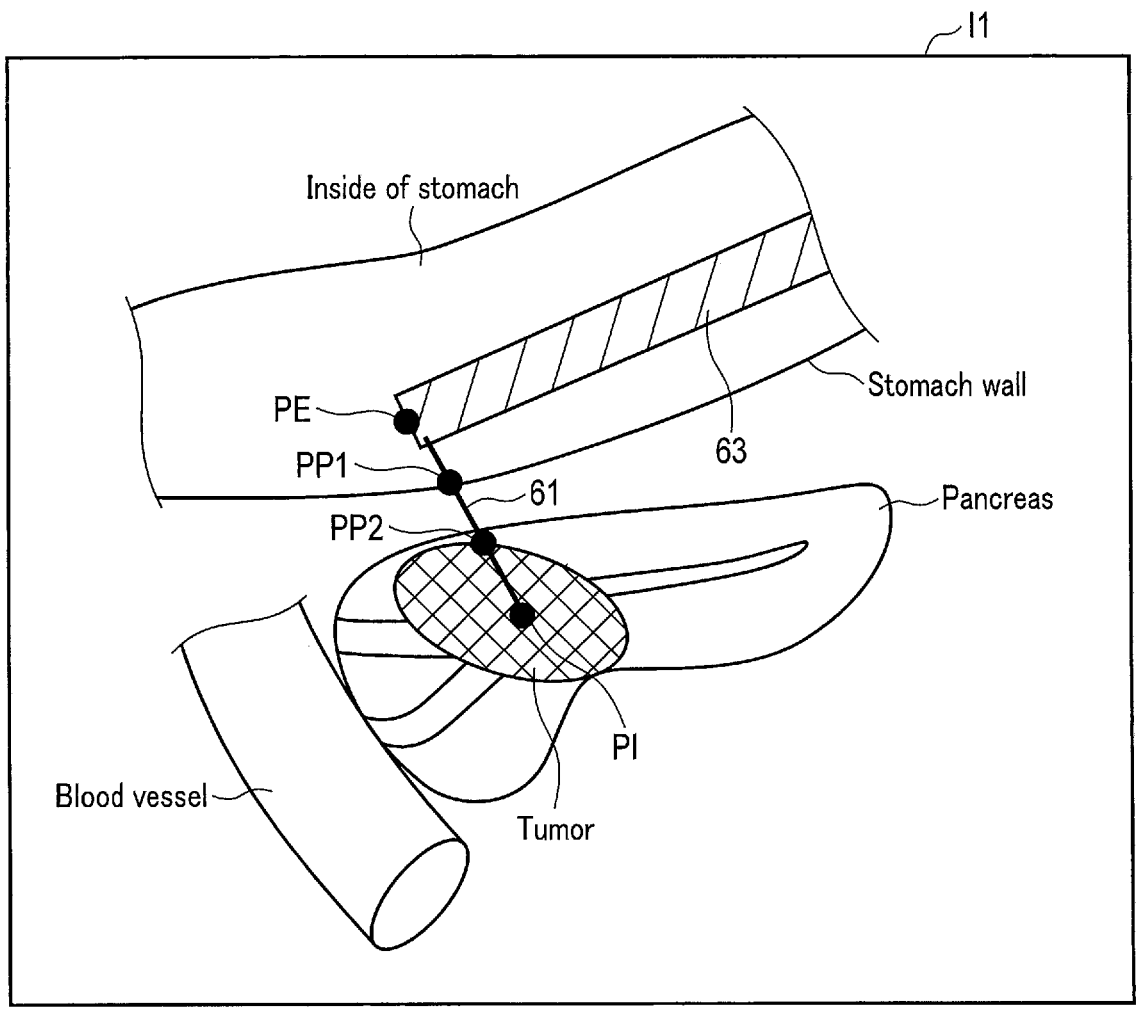
FIG. 6 is a diagram showing an example of a medicament administration plan image.

FIG. 6 is a diagram showing an example of a medicament administration plan image I1. As shown in FIG. 6, the medicament administration plan image I1 shows the tumor and anatomical tissue specified in step SC2-1. Although the medicament administration plan image I1 is a three-dimensional in actuality, it is shown as a two-dimensional image in FIG. 6 for convenience.

First, the processing circuitry 31 determines, based on the tumor location, whether an injection syringe having a needle for injecting a medicament from the skin surface or the ultrasonic endoscope 5 having a puncture needle for injecting a medicament within the body should be used as a medicament injection device. As an example, the processing circuitry 31 determines whether an injection syringe having a needle or the ultrasonic endoscope 5 having a puncture needle should be used in accordance with the distance between the tumor and the skin surface. For example, if the distance between the tumor and the skin surface is short, it is determined that an injection syringe having a needle is used; on the other hand, if the distance is longer than a threshold, it is determined that the ultrasonic endoscope 5 having a puncture needle is used. The threshold can be set at a discretionary value in accordance with the length, etc. of the puncture needle. As another example, the processing circuitry 31 determines whether an injection syringe having a needle or the ultrasonic endoscope 5 having a puncture needle should be used in accordance with a type of the tumor-bearing anatomical tissue. For example, a LUT in which a flag indicating the use of the injection syringe having a needle or a flag indicating the use of the ultrasonic endoscope 5 having a puncture needle is associated with the name or symbol of the anatomical tissue (hereinafter, a "used device table") is stored in the memory apparatus 39. The processing circuitry 31 specifies the name or symbol of the anatomical tissue in which a target tumor occurs with the above-described method, inputs the specified name or symbol into the used device table, outputs a flag associated with the name or symbol, and thereby determines which of the injection syringe having a needle or the ultrasonic endoscope 5 having a puncture needle is used.

If the ultrasonic endoscope 5 having a puncture needle is used, the processing circuitry 31 determines a luminal organ near the tumor as tissue into which the ultrasonic endoscope 5 is inserted (hereinafter, an "insertion-targeted tissue") based on the forms and properties of the anatomical value specified in step SC2-1. For example, if a tumor occurs in the pancreas, since the stomach, which is a luminal organ, exists near the pancreas, the stomach is determined as an insertion-targeted tissue. The insertion-targeted tissue may be determined by image recognition performed by the processing circuitry 31 or determined manually by a technician, etc. via the input interface 37.

Next, the processing circuitry 31 determines targeted positions based on a positional relationship between the tumor and the insertion-targeted tissue. For example, the processing circuitry 31 determines, as targeted positions, a tissue piercing point PP1, a tumor piercing point PP2, and a medicament injection point PI. The medicament injection point PI is a position in the tumor which is a medicament administration target, and it is a targeted position for the needle point of the puncture needle. The medicament injection point PI may be automatically set at the center point or the gravity point, etc. of a tumor, or may be manually set by a technician via the input interface 37. The tissue piercing point PP1 is a position at which the puncture needle is inserted into the insertion-targeted tissue. The tumor piercing point PP2 is a position at which the puncture needle is inserted into a tumor targeted for medicament administration, the tumor being located deeper than the insertion-targeted tissue. For example, a position located within a range around the medicament injection point PI approachable for the inserted puncture needle is determined as the tissue piercing point PP1. At this time, the position of the tissue piercing point PP1 may be limited based on the attachment angle of the puncture needle with respect to the insertion unit. The tumor piercing point PP2 is set to the point where a line extending from the straight line connecting the tissue piercing point PP1 to the medicament injection point PI intersects the tumor surface. In a case where the tumor is present on a wall surface of the insertion-targeted tissue, for example, the tissue piercing point PP1 and the tumor piercing point PP2 may be set at the same position.

Subsequently, the processing circuitry 31 sets an endoscope-targeting arrival point PE as another targeted position. The endoscope-targeting arrival point PE is a position at which the distal end of the insertion unit of the ultrasonic endoscope 5 should be situated in a luminal organ so as to allow the puncture needle to be inserted at the tissue piercing point PP1 or the tumor piercing point PP2. The endoscope-targeting arrival point PE is preferably set at, for example, a discretionary position in the stomach on the line extending from the straight line connecting the tissue piercing point PP1 to the tumor piercing point PP2, and more specifically, a position approachable for the distal end of the insertion unit of the ultrasonic endoscope 5. The endoscope-targeting arrival point PE may be set by the processing circuitry 31 in accordance with the algorithm or set manually by a technician, etc. via the input interface 37. The order of determining the tissue piercing point PP1, the tumor piercing point PP2, the medicament injection point PI, and the endoscope-targeting arrival point PE is not limited to the above-described example, and these points can be determined in any order.

As shown in FIG. 6, an insertion unit mark 63 imitating the insertion unit and a puncture needle mark 61 imitating the puncture needle are superposed on the medicament administration plan image I1. The insertion unit mark 63 is situated so that the distal end is located at the endoscope-targeting arrival point PE, and the puncture needle mark 61 is situated so that the needle point is located at the medicament injection point PI and the other end of the puncture needle is located at the attachment part of the insertion unit. By superposing the insertion unit mark 63 and the puncture needle mark 61 on the medicament administration plan image I1 in the above-described manner, it is possible to visually understand the positional relationship between the ultrasonic endoscope 5 and those multiple targeted positions.

The processing circuitry 31 may determine, as a medicament administration plan, an injection amount of medicament based on patient's information or state or a state of a tumor. If the medicament is a carcinostatic, the injection amount is determined based on measurement values of the patient's body and measurement values of biological matter. Specifically, a body surface area calculated from the patient's height and weight, and measurement values of a patient's biomarkers, such as blood platelet and white blood cells. For example, the injection amount of a carcinostatic should be calculated in such a manner that the amount is increased if the body surface area of a patient is larger and decreased if the number of white blood cells is reduced. The amount of injection may be set by the processing circuitry 31 in accordance with the algorithm or manually set by a technician, etc. via the input interface 37. The processing circuitry 31 may set, as the medicament administration plan, the injection speed in accordance with a predetermined algorithm or manually set by a technician, etc. via the input interface 37.

After step SC3-1, the processing circuitry 31, through realization of the display controlling function 315, displays the medicament administration plan produced in step SC3-1 (step SC4-1). The medicament administration plan is displayed on the display device 35. The processing circuitry 31 displays, as a medicament administration plan, the medical image obtained in step SC1-1 with the medicament administration plan parameters, such as the targeted positions, etc. determined in step SC3-1.

Figure 7:
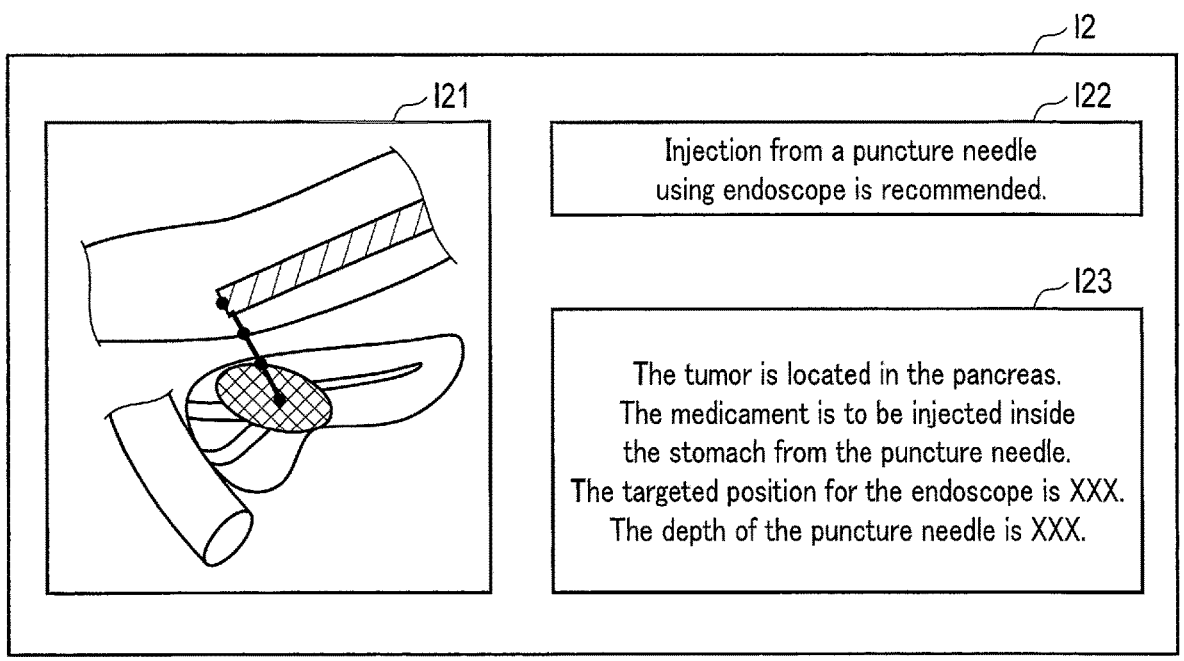
FIG. 7 is a diagram showing an example of a display window for a medicament administration plan image.

FIG. 7 is a diagram showing an example of a display window I2 for a medicament administration plan image. The display window I2 includes a medicament administration plan image I21, a display section I22 for an administration technique type, and a display section I23 for the medicament administration plan parameters. The medicament administration plan image I21 is the same as the medicament administration plan image generated in step SC3-1. The medicament administration plan image I21 is an image obtained by adding the medicament administration plan parameters, such as a tumor position and targeted positions for the ultrasonic endoscope 5, to the medical image obtained in step SC1-1. The display section I22 displays a message regarding whether an injection syringe having a needle or the ultrasonic endoscope 5 having a puncture needle is used, based on the determination in step SC3-1. For example, if it is determined that the ultrasonic endoscope 5 having a puncture needle is used, a message indicating, for example, "Injection from a puncture needle using an endoscope is recommended", is displayed. The display section I23 displays information regarding the medicament administration plan parameters determined in step SC3-1. For example, the following may be displayed: "The tumor is located in the pancreas" as information relating to the medicament administration plan parameter "tumor position"; "The medicament is to be injected inside the stomach from the puncture needle" as information regarding the medicament administration plan parameter "tissue piercing point"; "The targeted position for the endoscope is XXX" as information relating to the medicament administration plan parameter "endoscope-targeting arrival point"; and "The puncture depth of the puncture needle is XXX" as information regarding the medicament administration plan "medicament injection point".

The medicament administration plan can show a technician, etc. a positional relationship among the targeted positions for the ultrasonic endoscope 5, the tumor, and the peripheral anatomical tissue inside the patient's body; thus, the technician, etc. can easily and clearly imagine a path of invasion of a medicament injection device such as the ultrasonic endoscope 5 in advance. The medicament administration plan can thus improve certainty of the injection administration technique.

In the foregoing descriptions, the medicament injection point is described as a point set at a tumor. However, the present embodiment is not limited thereto. For example, if there is a blood vessel that nourishes a tumor, the medicament may be administered to the tumor through injection of the medicament into the blood vessel. Specifically, through the realization of the medicament administration plan producing function 312, the processing circuitry 31 searches for an area of a specific blood vessel that connects to a tumor shown in the medical image, and if the specific blood vessel area is specified, a medicament administration plan for injecting a medicament into the blood vessel is produced. In more detail, it is preferable that a medicament injection point be set on this blood vessel, and a tissue piercing point and an endoscope-targeting arrival point, etc. be determined in accordance with the position of the set medicament injection point.

The processing circuitry 31 may determine, as a medicament administration plan, a timing for medicament injection based on patient's biological waveforms, such as a spirogram and an electrocardiogram. Assume that the biological waveforms are those collected by various measurement devices, along with medical imaging by the medical image diagnosis apparatus 1. For example, if a spirogram is used, the processing circuitry 31 determines based on the spirogram a respiration phase in which body motion due to respiration is relatively small. The determined respiration phase is set as an injection timing. If an electrocardiogram is used, the processing circuitry 31 determines based on the electrocardiogram a respiration phase in which body motion due to a heart beat is relatively small or large. The determined cardiogram phase is set as an injection timing. For example, when a medicament is injected into a blood vessel, injection timing is preferably determined using the electrocardiogram.

Next, the second embodiment example of the medicament administration plan producing process will be described.

Figure 8:
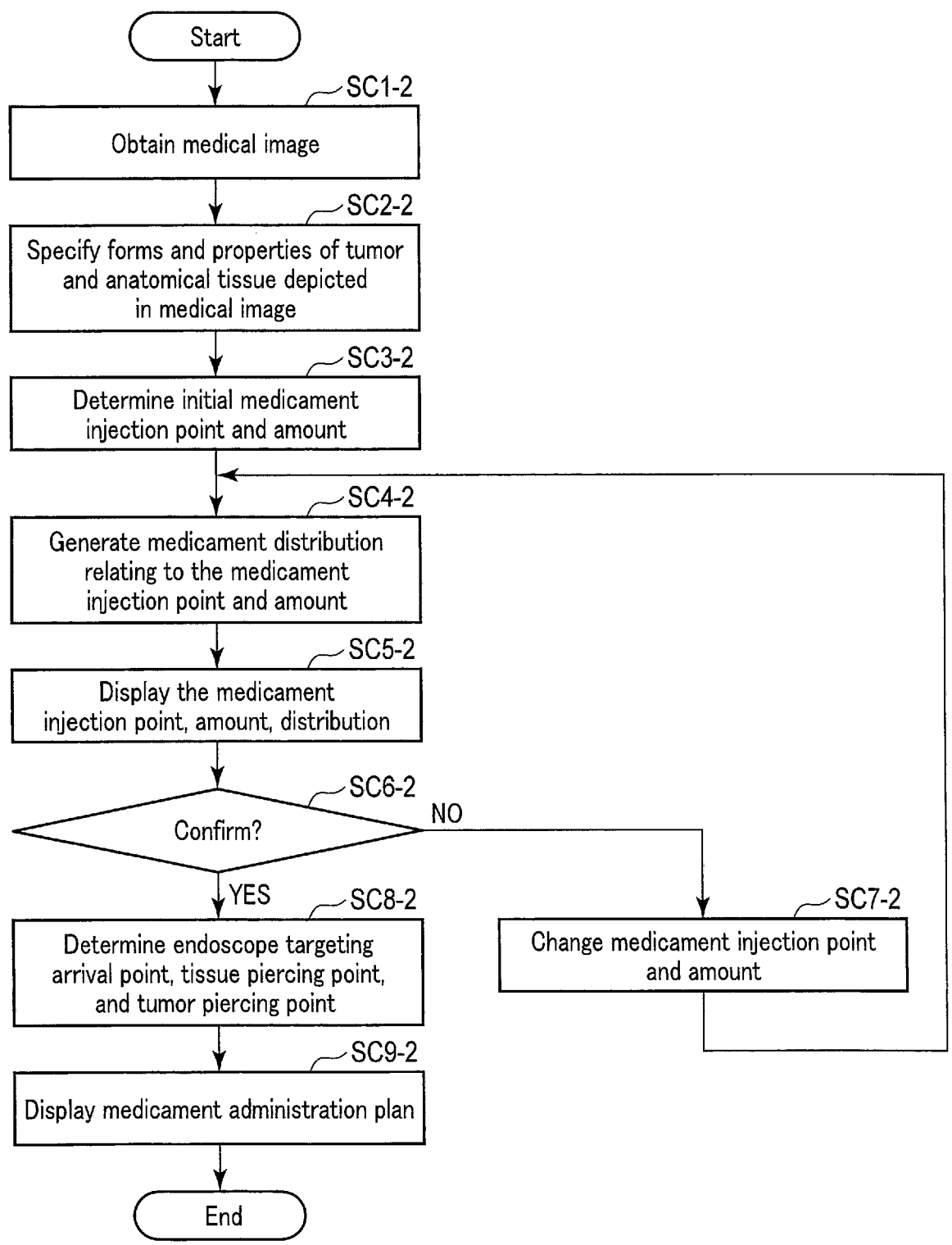
FIG. 8 is a diagram showing a flow of a second embodiment of a medicament administration plan producing process by a medicament administration planning apparatus.

FIG. 8 is a diagram showing a flow of the second embodiment example of the medicament administration plan producing process by the medicament administration planning apparatus 3. As shown in FIG. 8, the processing circuitry 31 obtains a medical image through the realization of the obtainment function 311 (step SC1-2). Step SC1-2 is similar to step SC1-1 in FIG. 5.

After step SC1-2, the processing circuitry 31, through the realization of the medicament administration plan producing function 312, specifies forms and properties of a tumor and anatomical tissue shown in the medical image obtained in the step SC1-2 (step SC2-2). Step SC2-2 is similar to step SC2-1 in FIG. 5.

After step SC2-2, the processing circuitry 31, through the realization of the medicament administration plan producing function 312, determines an initial medicament injection point and an initial medicament injection amount for the medicament (step SC3-2). It suffices for the initial medicament injection point to be set at a discretionary location, such as the center point or gravity point of a tumor specified in step SC2-2. If the medicament is a carcinostatic, it suffices for the initial medicament injection point to be determined based on information or a status of the patient or a state of the tumor, as described previously. The initial medicament injection point and the initial medicament injection amount may be discretionarily set at a position and an amount through the input interface 37 by a technician, etc.

After step SC3-2, the processing circuitry 31, through the realization of the medicament distribution generating function 313, generates a medicament distribution relating to the medicament injection point and the medicament injection amount determined in step SC3-2 (step SC4-2). In step SC4-2, the processing circuitry 31 generates a medicament distribution relating to a tumor based on, for example, the forms and properties of the tumor and the anatomical tissue shown in the medical image, the medicament injection point, and the medicament injection amount.

Figure 9:
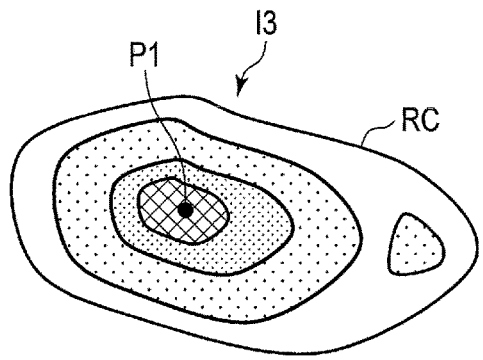
FIG. 9 is a drawing schematically showing an example of medicament distribution relating to a tumor.

FIG. 9 is a drawing schematically showing a medicament distribution I3 relating to a tumor RC. As shown in FIG. 9, the medicament distribution I3 represents a spatial distribution of a predicted administration amount of medicament in the tumor RC in the case where the medicament of the medicament injection amount determined in step SC3-2 is injected to the tumor RC from the medicament injection point P1 determined in step SC3-2.

The processing circuitry 31 simulates a flow in the tumor of the medicament injected in the medicament injection amount from the medicament injection point, based on the forms and properties of the tumor and the anatomical tissue shown in the medical tissue, the medicament injection amount, and the medicament injection point. For example, the processing circuitry 31 performs blood flow dynamic analysis on the tumor and the peripheral anatomical tissue based on a contrast CT image, a contrast MR image, an ultrasonic Doppler image, a nuclear medical image, etc. of a patient, and calculates a blood flow parameter for evaluating blood flow dynamics, such as a blood inflow amount and a blood outflow amount of each pixel. On the assumption that the dynamics of the blood flow are similar to those of the medicament, the processing circuitry 31 calculates, for each pixel, a medicament parameter for evaluating the dynamics of the medicament by adding or multiplying a discretionary coefficient to or by the blood flow parameter. Then, the processing circuitry 31 simulates a flow of the medicament injected in the tumor by the medicament injection amount from the medicament injection point based on the medicament parameter, and generates, as a medicament distribution, a spatial distribution of the amount of medicament administered to each pixel.

After step SC4-2 is performed, the processing circuitry 31, through the realization of the display controlling function 315, displays the medicament injection point and medicament injection amount determined in step SC3-2 and the medicament distribution generated in step SC4-2 (step SC5-2). The display windows for the medicament injection point, the medicament injection amount, and the medicament distribution are displayed on the display device 35.

Figure 10:
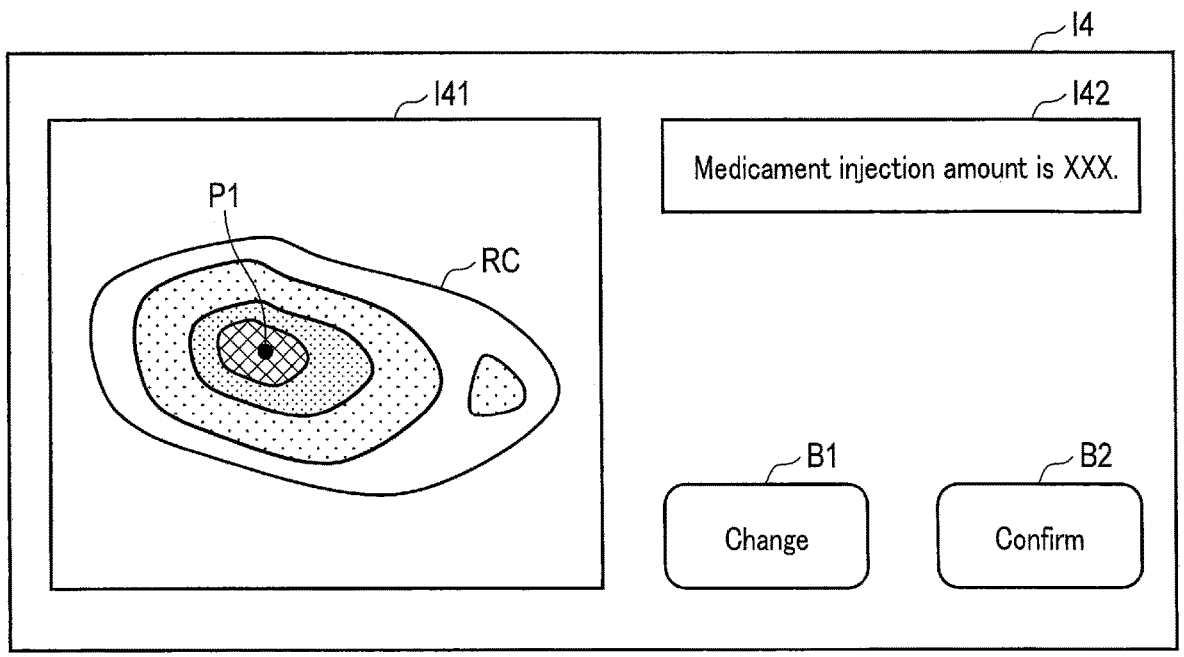
FIG. 10 is a diagram showing an example of a display window for medicament distribution.

FIG. 10 is a diagram showing an example of a display window I41 for the medicament distribution I41. As shown in FIG. 10, the display window I4 displays the medicament distribution I41, the display section I42 for the medicament injection amount, the change button B1, and the confirmation button B2. The medicament distribution I41, similarly to the medicament distribution shown in FIG. 9, represents a spatial distribution of an amount of medicament administered to the tumor RC in the case where the medicament injection amount, which is determined in step SC3-2, of the medicament is injected into the tumor RC from the medicament injection point P1 determined in step SC3-2. The medicament distribution I41 is displayed with colors in accordance with an amount of administered medicament. A mark indicating the medicament injection point P1 is superposed on the medicament distribution I41. In the display section I42, the medicament injection amount determined in step SC3-2 is displayed. The change button B1 is a GUI button that instructs a change of the medicament injection point and the medicament injection amount. The confirmation button B2 is a GUI button that instructs a confirmation of the medicament injection point and the medicament injection amount. Through the display of the medicament distribution I41, the injection point P1, and the medicament injection amount, a technician, etc. is able to visually understand the distribution aspects of the medicament in the case when the medicament is injected only in the medicament injection amount from the medicament injection point P1.

After step SC5-2, the processing circuitry 31 waits for the determination of the medicament injection point and the medicament injection amount (step SC6-2). For example, if a technician, etc. determines that the medicament distribution aspect is not desirable, he or she presses the change button B1 via the input interface 37. When the change button B1 is pressed (No in step SC6-2), the processing circuitry 31, through the realization of the medicament administration plan producing function 312, changes the medicament injection point and the medicament injection amount (step SC7-2). The changed injection point and the changed amount of the medicament injection amount may be predetermined or may be discretionarily set by a technician, etc. via the input interface 37. Thereafter, the processing circuitry 31 repeats the process from step SC4-2 to step SC7-2 until the technician, etc. has pressed the confirmation button B2 via the input interface 37 in step SC6-2.

If the confirmation button is pressed in step SC6-2 (Yes in step SC6-2), the processing circuitry 31, through the realization of the medicament administration plan producing function 312, determines the targeted positions of the ultrasonic endoscope 5 and the puncture point of the puncture needle (step SC8-2). In step SC8-2, the processing circuitry 31 determines the endoscope-targeting arrival point, the tissue piercing point, and the tumor piercing point based on the confirmed injection point, and the forms and properties of the tumor and the anatomical tissue determined in step SC2-2. The endoscope-targeting arrival point, the tissue piercing point, and the tumor piercing point can be determined by the same method as that of step SC3-1 in FIG. 5.

After step SC8-2, the processing circuitry 31, through the realization of the display controlling function 315, displays a medicament administration plan (step SC9-2). The medicament administration plan displayed in step SC9-2 is the same as that shown in FIG. 7. The medicament distribution confirmed in step SC6-2 may be superposed on the medicament administration plan image. The medicament administration plan is stored in the memory apparatus 39.

Thus, the second embodiment example of the medicament administration plan producing process is finished.

As described in the above, the processing circuitry 31 in the second embodiment example generates multiple distributions while changing the medicament injection point and the medicament injection amount, and determines, as the medicament administration plan, a specific medicament injection point and a specific injection amount corresponding to a specific medicament distribution among the multiple generated medicament distributions. In the case of the embodiment example shown in FIG. 8, the specific medicament distribution is a medicament distribution designated by a technician, etc. in step SC6-2. However, the embodiment is not limited to this example, and a specific medicament distribution may be automatically selected from multiple medicament distributions based on predetermined determination criteria. The generation and display of a medicament distribution can ensure accuracy of the medicament administration plan parameters, such as the medicament injection point, the medicament injection amount, the endoscope-targeting arrival point, the tissue piercing point, and the tumor piercing point.

The second embodiment example of the medicament administration plan generating process can be modified in various ways. For example, in step SC9-2, the processing circuitry 31 may superpose the medicament distribution with the initial dose distribution and display the superposition on the display device 35.

Figure 11:
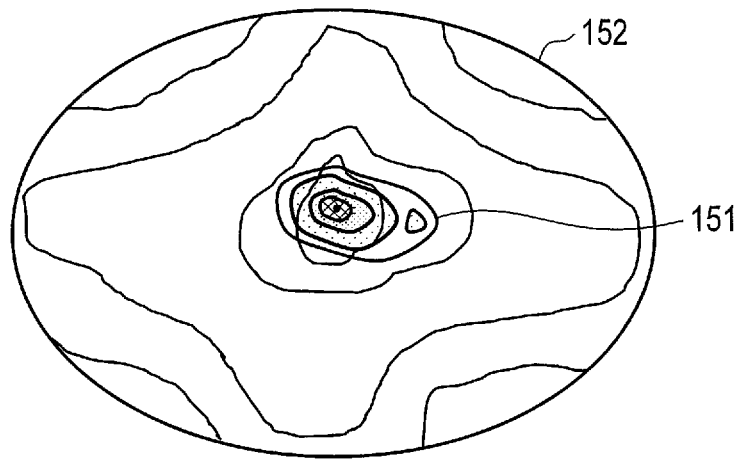
FIG. 11 is a diagram showing an example of a superposed display of medicament distribution and dose distribution.

FIG. 11 is a diagram showing an example of a superposed display of the medicament distribution I51 and the initial dose distribution I52. As shown in FIG. 11, each pixel of the medicament distribution I51 is displayed in a color in accordance with an administered medicament amount, and contour lines are displayed for respective predetermined administered medicament amounts. In the initial dose distribution I52, each pixel is displayed in a color in accordance with an administered dose, and contour lines are displayed for respective predetermined administered doses. On the tumor area in the initial dose distribution I52, the medicament distribution I51 relating to the tumor area is superposed. In order to improve viewability of the medicament distribution I51 and the initial dose distribution I52, the initial dose distribution I52 may be displayed with a relatively high transparency level, and the medicament distribution I51 may be displayed with a relatively low transparency level, for example. Alternately, either one of the medicament distribution I51 and the initial dose distribution I52 may be displayed in color and the other may be displayed in black and white. The superposed display of the medicament distribution I51 and the initial dose distribution I52 makes it easy to check the administered medicament amount and the initial administered dose at the same location.

Furthermore, the processing circuitry 31 may output information with which whether or not at least one of the medicament distribution or the dose distribution exceeds an allowance can be identified. For example, the processing circuitry 31 may compare an administered medicament amount with an allowance for each pixel of the medicament distribution, and may display a pixel that exceeds the allowance with a visual emphasis. As another example, the processing circuitry 31 may compare an administered amount with an allowance for each pixel of the dose distribution, and may display a pixel that exceeds the allowance with a visual emphasis. In this case, the emphasized pixel is an example of "identifiable information". By emphasizing a pixel that exceeds an allowance, it is possible to visually understand which part is not allowable. The user may manually correct the administered medicament amount or the administered dose of such a non-allowable part.

Furthermore, the processing circuitry 31 may display a superposition of the dose distribution and the medicament distribution, along with the identifier information. The processing circuitry 31 may display the dose distribution and the medicament distribution side by side, together with the identifiable information.

The processing circuitry 31, through the realization of the medication-combined radiotherapy plan generating function 314, may increase or reduce the administered dose allocated to each pixel of the dose distribution relating to the patient, based on the administered medicament amount allocated to each pixel of the medicament distribution. For example, if the medicament is a radiosensitizer or a carcinostatic, the administered dose in a region where the administered medicament amount is larger than a threshold may be reduced, or the administered dose in a region where the administered medicament amount is smaller than a threshold may be increased, or the administered dose in a region where the administered medicament amount is larger than a first threshold may be reduced and the administered dose in a region where the administered medicament amount is smaller than a second threshold may be increased. Such reduction and increase in the administered dose in accordance with the administered medicament amount makes it possible to optimize potentiation in the combined use of the medicament injection and the radiotherapy.

The processing circuitry 31, through the realization of the medicament distribution generating function 313, may increase or decrease the administered medicament amount allocated to each pixel of the dose distribution, based on the administered dose allocated to each pixel of the dose distribution. For example, if the medicament is a radiosensitizer or a carcinostatic, the administered medicament amount in a region where the administered dose is larger than a threshold may be reduced, or the administered medicament amount in a region where the administered dose is smaller than a threshold may be increased, or the administered medicament amount in a region where the administered dose is larger than a first threshold may be reduced and the administered medicament amount in a region where the administered dose is smaller than a second threshold may be increased. In a case where the administered dose cannot be increased under the restrictions on the dose, etc. contrary to the need for the increase, the administered medicament amount may be increased. The reduction and increase of the administered medicament amount may be achieved by reducing or increasing the medicament injection amount while the medicament injection point is being fixed, or by reducing or increasing both the medicament injection amount and the medicament injection point. Such reduction and increase of the administered medicament amount in accordance with the administered dose makes it possible to optimize potentiation in the combined use of the medicament injection and the radiotherapy.

A medication-combined radiotherapy plan is generated based on the medicament distribution and the initial dose distribution obtained by the foregoing various embodiment examples. In the following, the medication-combined radiotherapy plan producing process by the medicament administration planning apparatus 3 will be described.

Figure 12:
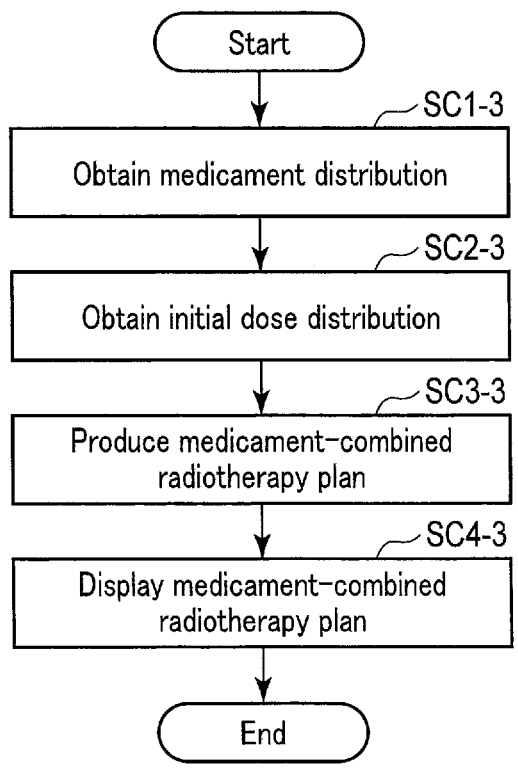
FIG. 12 is a diagram showing a flow of a process of producing a medicament administration plan by a medicament administration planning apparatus.

FIG. 12 is a diagram showing a flow of the process of producing a medicament administration plan by the medicament administration planning apparatus 3. As shown in FIG. 12, the processing circuitry 31 obtains medicament distributions through the realization of the obtainment function 311 (step SC1-3). Typically, the processing circuitry 31 obtains a medicament distribution generated by the medicament distribution generating function 313. A medicament distribution generated by one of the methods in the above-described embodiment examples is obtained.

After step SC1-3, the processing circuitry 31, through the realization of the obtainment function 311, obtains an initial dose distribution (step SC2-3). Typically, the processing circuitry 31 obtains an initial dose distribution generated by the radiotherapy planning apparatus 2.

After step SC2-3, the processing circuitry 31, through the realization of the medication-combined radiotherapy plan producing function 314, produces a medication-combined radiotherapy plan based on the medicament distribution obtained in step SC1-3 and the initial dose distribution obtained in step SC2-3 (step SC3-3). In step SC3-3, the processing circuitry 31 changes at least one of the medicament distribution or the initial dose distribution for an area where the medicament distribution overlaps the initial dose distribution, and produces the radiotherapy plan based on the changed distributions.

The medication-combined radiotherapy plan includes a medicament administration plan and a radiotherapy plan for a tumor administered with a medicament based on the medicament administration plan. As the medicament administration plan included in the medication-combined radiotherapy plan, one produced by one of the methods in the foregoing embodiment examples is preferably used in the medication-combined radiotherapy plan. Alternately, the medicament administration plan may be corrected in accordance with a medicament distribution changed in accordance with an initial dose distribution. In this case, the processing circuitry 31 changes the medicament distribution based on the initial dose distribution and produces a medication-combined radiotherapy plan based on the changed medicament distribution and the initial dose distribution, as described above. In other words, the medicament injection point, the medicament injection amount, the endoscope-targeting arrival point, the tissue piercing point, and the tumor piercing point are changed in accordance with the changed medicament distribution.

As the radiotherapy plan included in the medication-combined radiotherapy plan, one produced by one of the methods in the foregoing embodiment examples is preferably used in the medication-combined radiotherapy plan.

Alternately, the radiotherapy plan may be corrected in accordance with the dose distribution changed according to the medicament distribution (confirmed dose distribution). In this case, the processing circuitry 31 changes the initial dose distribution based on the medicament distribution and generates a confirmed dose distribution, and produces a medication-combined radiotherapy plan based on the confirmed dose distribution and the medicament distribution, as described above. In other words, the number of irradiation gates, an irradiation angle, a radiation intensity, a collimator opening degree, and a wedge filter are changed in accordance with the confirmed dose distribution.

After step SC3-3 is performed, the processing circuitry 31, through the realization of the display controlling function 315, displays the medication-combined radiotherapy plan produced in step SC3-3 (step SC4-3). In step SC4-3, the processing circuitry 31 displays the medication-combined radiotherapy plan on the display device 35. As the medication-combined radiotherapy plan, an image showing the confirmed dose distribution or the medicament distribution may be displayed, and a character or a number, etc. that shows the medicament administration plan or the medicament distribution may be displayed. A user can check the content of the medication-combined radiotherapy plan through the display thereof.

Thus, the process of producing a medication-combined radiotherapy plan is finished.

The processing circuitry 31 may produce a plurality of medication-combined radiotherapy plans differing from each other based on the medicament distribution and the dose distribution, and may display a list of those produced medication-combined radiotherapy plans.

Figure 13:
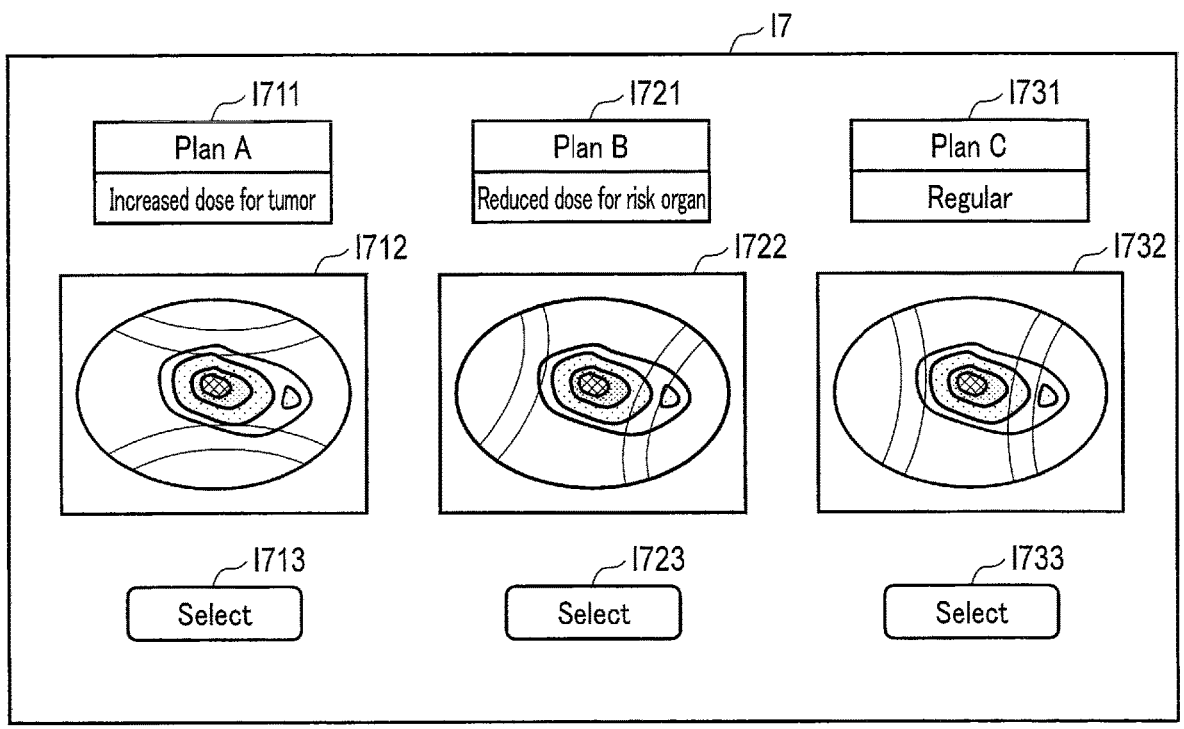
FIG. 13 is a diagram showing an example of a display window for a list of medication-combined radiotherapy plans.

FIG. 13 is a diagram showing an example of the display window I7 for a list of medication-combined radiotherapy plans. The display window I7 is displayed on the display device 35, etc. In FIG. 13, three medication-combined radiotherapy plans are shown as an example. The display window I7 displays labels I711, I721, and I731 for respective medication-combined radiotherapy plans, side by side. Each of the labels I711, I721, and I731 may be a symbol of each medication-combined radiotherapy plan, such as "plan A", "plan B", or "plan C", or a string of characters that represents a feature of each medication-combined radiotherapy plan, such as "increased dose for tumor", "reduced dose for risk organ", or "standard".

As shown in FIG. 13, as each medication-combined radiotherapy plan, superposed images 1712, 1722, and 1732, in which the confirmed dose distribution and the medicament distribution are superposed, are displayed side by side. For example, in the case of plan A, if the administered medicament amount is relatively small in a tumor area targeted for treatment, the administered dose in the tumor area is increased compared to the administered dose in the initial dose distribution. In the case of plan B, if the administered medicament amount is relatively large in a tumor area targeted for treatment, the administered dose in the tumor area is reduced compared to the administered dose in the initial dose distribution. In the case of plan C, the same dose distribution as the initial dose distribution is used as the confirmed dose distribution. The display of the superposed images 1712, 1722, and 1732 side by side allows the user to visually understand the differences in the confirmed dose distribution between the plans. In addition to the superposed images of the configured dose distribution and the medicament distribution, the parameters of the medicament administration plan or the radiotherapy plan may also be displayed.

As shown in FIG. 13, the select buttons I713, I723, and I733 for each medication-combined radiotherapy plan are displayed side by side on the display window I7. If one of the select buttons I713, I723, and I733 is pressed by a user via the input interface 37, the corresponding medication-combined radiotherapy plan is selected. A support for the medication-combined radiotherapy will be performed by the radiotherapy support system in accordance with the selected medication-combined radiotherapy plan.

Next, the medicament administration guiding apparatus 4 used in step SD shown in FIG. 2 is described.

Figure 14:
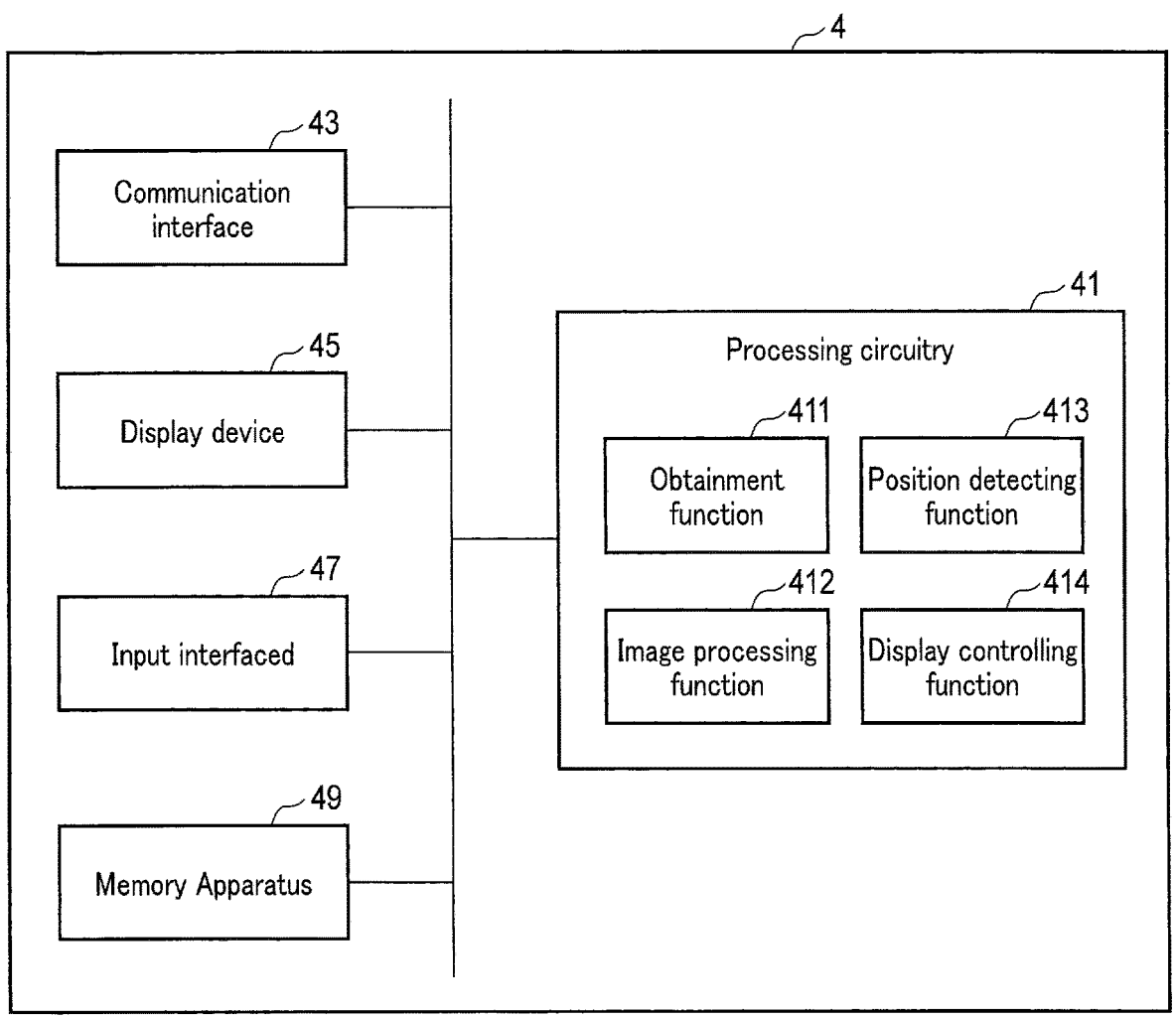
FIG. 14 is a diagram showing an exemplary configuration of a medicament administration guiding apparatus shown in FIG. 1.

FIG. 14 is a diagram showing an exemplary configuration of the medicament administration guiding apparatus 4. As shown in FIG. 14, the medicament administration guiding apparatus 4 includes processing circuitry 41, a communication interface 43, a display device 45, an input interface 47, and a memory apparatus 49. The processing circuitry 41 is an example of a processing unit; the communication interface 43 is an example of a communication unit; the display device 45 is an example of a display device; the input interface 47 is an example of an input unit; and the memory apparatus 49 is an example of a memory unit.

The processing circuitry 41 has a processor. The processor activates various programs installed on the memory apparatus 49, etc. and thereby realizes the obtainment function 411, the image processing function 412, the position detecting function 413, and the display controlling function 414. Note that the embodiment is not limited to the case in which the respective functions 411 to 414 are realized by single processing circuitry 41. Processing circuitry may be composed by combining a plurality of independent processors, and the respective processors may execute programs, thereby realizing the functions 411 to 414. The acquisition function 411 is an example of an obtainment unit; the image processing function 412 is an example of an image processing unit; the position detecting function 413 is an example of a position detecting unit; and the display controlling function 414 is an example of a display unit.

Through the realization of the obtainment function 411, the processing circuitry 41 obtains various information items. Specifically, the processing circuitry 41 obtains a medical image generated by the medical image diagnosis apparatus 1, a radiotherapy plan produced by the radiotherapy planning apparatus 2, a medicament administration plan produced by the medicament administration planning apparatus 3, an ultrasonic image and an optical image generated by the ultrasonic endoscope 5, and the like. A form of the acquisition is not limited to direct acquisition from each apparatus; information received from an apparatus may be stored in the memory apparatus 49 and the information may then be obtained from the memory apparatus 49.

The processing circuitry 41, through the realization of the image processing function 412, performs image processing on various images obtained by the obtainment function 411.

The processing circuitry 41, through the realization of the position detecting function 413, detects a current position of the ultrasonic endoscope 5.

Through the realization of the display controlling function 414, the processing circuitry 41 displays various information items via the display device 45. For example, the processing circuitry 41 displays the ultrasonic image and the optical image generated by the ultrasonic endoscope 5 and the medicament administration plan produced by the medicament administration planning apparatus 3. The processing circuitry 41 superposes guidance information for guiding the ultrasonic endoscope 5 to a targeted position on the ultrasonic image and/or optical image. The processing circuitry 41 displays the medicament administration plan image, which is a medical image to which a current location is added, and the ultrasonic image and/or the optical image, side by side.

The communication interface 43 is an interface for information communication among the medical image diagnosis apparatus 1, the radiotherapy planning apparatus 2, the medicament administration planning apparatus 3, and the ultrasonic endoscope 5 included in the radiotherapy support system 100, via wires or wirelessly.

The display device 45 displays various types of information through the display controlling function 414 of the processing circuitry 41. As the display device 45, for example, a liquid crystal display, a CRT display, an organic EL display, a plasma display, or any other display may be used as appropriate. The display device 45 may be a projector.

The input interface 47 accepts various kinds of input operations from a user, converts the accepted input operations to electric signals, and outputs the electric signals to the processing circuitry 41. Specifically, as the input interface 47, a mouse, a keyboard, a trackball, a switch, a button, a joystick, a touchpad, a touch panel display, etc. can be used as appropriate. The input interface 47 may be an audio input apparatus using audio signals from an input device that collects sound, such as a microphone. The input interface 47 may be a noncontact input circuit using an optical sensor. The input interface 47 outputs electric signals to the processing circuitry 41 according to an input operation. The input interface 47 may be an input device provided in an external computer connected to the system via a network, etc.

The memory apparatus 49 is a memory apparatus such as a ROM, a RAM, an HDD, an SSD, or an integrated circuit storage unit, etc., configured to store various kinds of information. The memory apparatus 49 stores, for example, the medical images, the medicament administration plan, the ultrasonic images, the optical images, etc. obtained by the obtainment function 411. The memory apparatus 49 may be not only the above-listed memory apparatuses, but also a driver that writes and reads various types of information in and from, for example, a portable storage medium such as a CD, a DVD, or a flash memory, or a semiconductor memory. The memory apparatus 49 may be provided in an external computer connected to the medicament administration guiding apparatus 4 via wires or wirelessly.

Next, a medicament administration guiding process by the medicament administration guiding apparatus 4 is described. The medicament administration guiding process is performed in accordance with the medicament administration plan, concurrently with the medicament administration technique by the ultrasonic endoscope 5. In the descriptions hereinafter, as shown in FIG. 3, assume that a tumor occurs in the pancreas, and an intra-body injection method is adopted as the medicament administration technique, by which a medicament is injected into a tumor using a puncture needle from the inside of the stomach.

FIG. 15 is a diagram showing a flow of the medicament administration guiding process by the medicament guiding apparatus 4. The medicament administration guiding process shown in FIG. 15 is triggered by an instruction input by a technician, etc. via the input interface 47 and started by the processing circuitry 41. Assume that, at the time when the medicament administration guiding process is started, the insertion unit of the ultrasonic endoscope 5 is inserted into the stomach and being directed to the endoscope-targeting arrival point. The ultrasonic endoscope 5 is generating an optical image by the optical imaging apparatus in the medicament administration guiding process and is supplying the optical image to the medicament administration guiding apparatus 4 in a real-time manner.

The processing circuitry 41 of the medicament administration guiding apparatus 4, through the realization of the position detecting function 413, is detecting the current position of the insertion unit of the ultrasonic endoscope 5 (hereinafter an "endoscope current position") in a real-time manner. The position detection method may be any kind of method, for example, position detection of the insertion unit based on a detection signal from a position sensor provided in the insertion unit, such as a global positioning system (GPS) sensor or a magnetic sensor, or position detection based on a result of positioning between a medical image of a patient and an optical image generated by the ultrasonic endoscope 5. As the medical image, a three-dimensional CT image or three-dimensional MR image, etc. that has been already used to produce the radiotherapy plan or the medicament administration plan may be used. If the ultrasonic endoscope 5 is generating an ultrasonic image by the ultrasonic imaging apparatus, the processing circuitry 41 may perform position detection based on a result of positioning between the ultrasonic image and the medical image.

As shown in FIG. 15, the processing circuitry 41, through the realization of the display controlling function 414, shows an invasion direction in the optical image (step SD1). In the medicament administration guiding process, the processing circuitry 41 displays the guidance window on the display device 45. In the guidance window, a mark indicating the invasion direction of the ultrasonic endoscope 5 is superposed on the optical image. The mark indicating the invasion direction is an example of guidance information.

Figure 16:
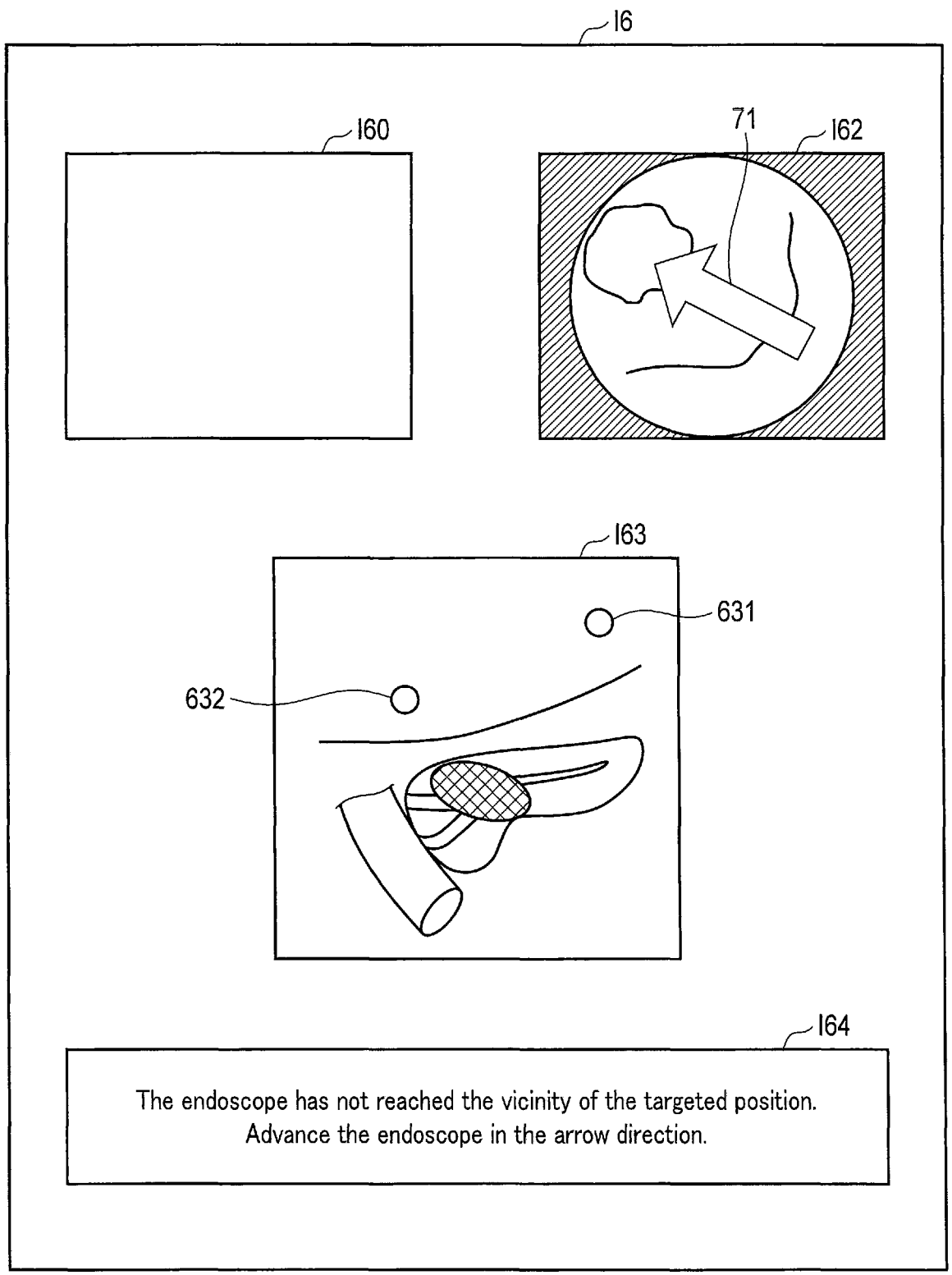
FIG. 16 is a diagram showing an example of a guide window displayed in step SD1.

FIG. 16 is a diagram showing an example of the guide window I6 displayed in step SD1. As shown in FIG. 16, the guide window I6 displays the optical image I62 and the medicament administration plan image I63. The optical image I62 is a video image generated by the ultrasonic endoscope 5 in a real-time manner. On the optical image I62, a mark 71 indicating the invasion direction of the ultrasonic endoscope 5 is superposed. A direction from the endoscope current position to the endoscope-targeting arrival point is determined as the invasion direction.

The medicament administration plan image I63 is an image obtained by adding the mark 631 indicating the endoscope current position and the mark 632 indicating the endoscope-targeting arrival point to the medical image. The position of the cross section or the point of view of the medicament administration plan image I63 is set so as to follow the current position of the ultrasonic endoscope 5. As shown in FIG. 16, the medicament administration plan image I63 is a cross-sectional image that includes both of the endoscope current position and the endoscope-targeting arrival point, for example. In this case, the processing circuitry 41 sets a cross section that includes both of the endoscope current position and the endoscope-targeting arrival point as a medical image, and generates a cross-sectional image relating to this cross section by a parallel projection method. The cross-sectional image may be generated so as to include only one of the endoscope current position or the endoscope-targeting arrival point. The mark 631 indicating the endoscope current position and the mark 632 indicating the endoscope-targeting arrival point are examples of guidance information.

The medicament administration plan image I63 is not limited to the above-described example; it may be a volume rendering image or a virtual endoscope image that includes an endoscope position. For example, the processing circuitry 41 sets the endoscope current position to the point of view, and generates a volume rendering image relating to this point of view by a parallel projection method. The processing circuitry 41 sets the endoscope current position to the point of view, and generates a virtual endoscope image relating to this point of view by a fluoroscopy imaging method.

The guide window I6 includes a display section I60 for an ultrasonic image and a display section I64 for a message. Since ultrasonic imaging has not yet been performed by the ultrasonic endoscope 5 by the time of performing step SD1, no ultrasonic image is displayed in the display section I60. Ultrasonic imaging may be performed by the ultrasonic endoscope 5 at the time of performing step SD1, and in this case, an ultrasonic image may be displayed in the display section I60.

The display section I64 displays a message that supports advancing of the ultrasonic endoscope 5 to a targeted position (hereinafter a "support message") in accordance with a distance between the endoscope current position and the endoscope-targeting arrival point (hereinafter a "difference in distance"). For example, if a difference in distance is larger than a threshold (hereinafter, a "first threshold"), the processing circuitry 41 displays a support message, for example "Not yet reached the vicinity of the targeted position. Advance the endoscope in the arrow direction". The first threshold may be set at a numerical value at a degree such that the tissue piercing point is visually identifiable in an optical image. Support messages may be categorized in advance in accordance with degrees of a difference in distance. The support messages are an example of guidance information.

After step SD1, the processing circuitry 41 determines whether or not the endoscope current position has reached the vicinity of the endoscope-targeting arrival point (step SD2). Specifically, in step SD2, the processing circuitry 41 determines whether or not the difference in distance is larger than the first threshold. If the difference in distance is larger than the first threshold (No in step SD2), the processing circuitry 41 proceeds to step SD1, and superposes a mark indicating the invasion direction of the ultrasonic endoscope 5 on the optical image in the guidance window. A technician, etc. looks at the optical image I62, the medicament administration plan image I63, and the support message as shown in FIG. 16 so as to be aware of the endoscope current position and the endoscope-targeting arrival point, so that he or she can advance the ultrasonic endoscope 5 toward the endoscope-targeting arrival point.

If the difference in distance is smaller than the first threshold (Yes in step SD2), the processing circuitry 41, through the realization of the display controlling function 414, displays the tissue piercing point in the optical image (step SD3). In step SD3, the processing circuitry 41 superposes a mark indicating the tissue piercing point on the optical image displayed in the guidance window. The mark indicating the tissue piercing point is an example of guidance information.

Figure 17:
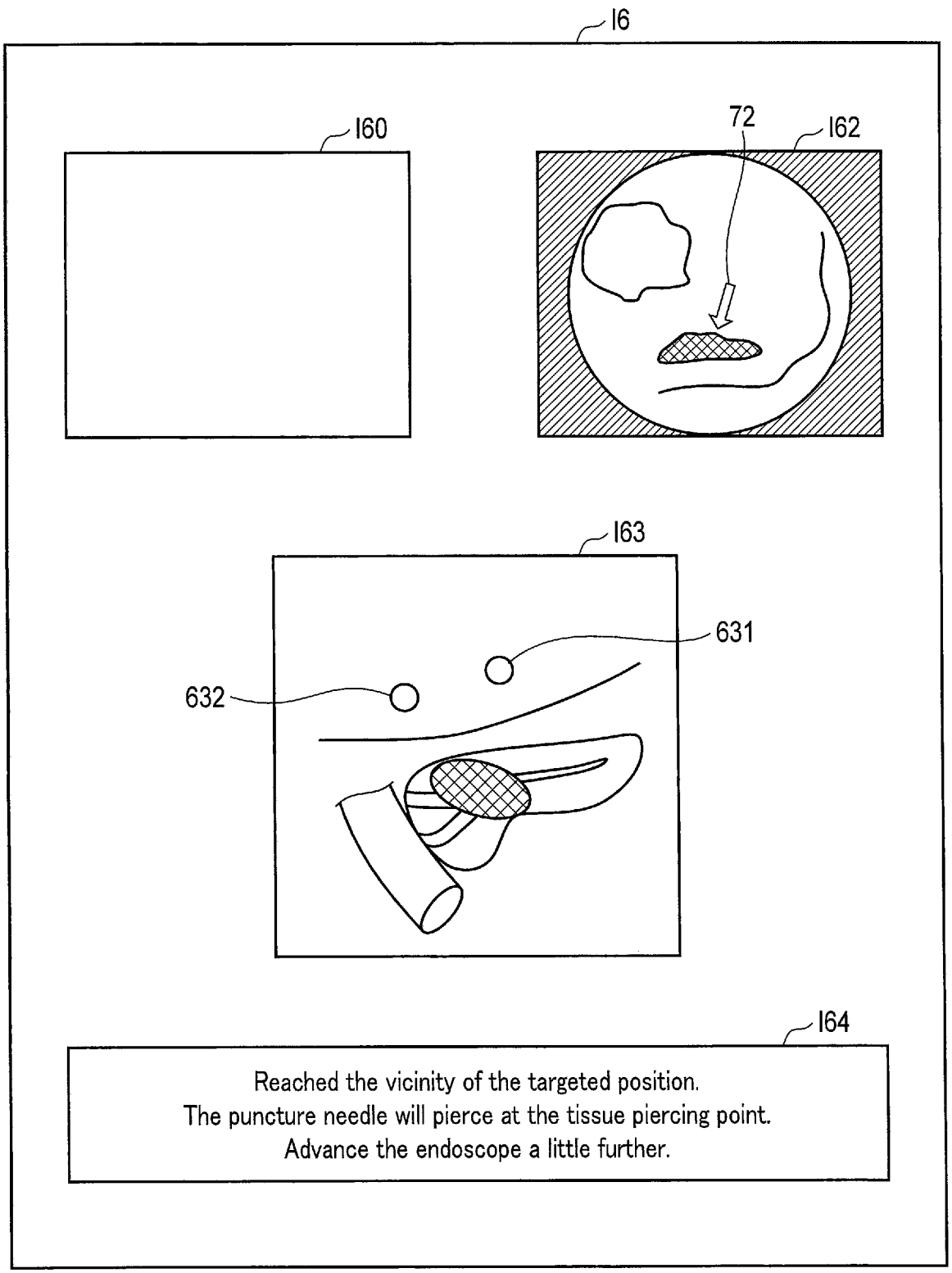
FIG. 17 is a diagram showing an example of a guide window displayed in step SD3.

FIG. 17 is a diagram showing an example of the guidance window I6 displayed in step SD3. As shown in FIG. 17, the guidance window I6 displays the optical image I62 and the medicament administration plan image I63. In step SD3, since the ultrasonic endoscope 5 is located near the endoscope-targeting arrival point, depending on the stage of the pancreas tumor, the pancreas tumor may have infiltrated the stomach wall, and the pancreas tumor will thereby be shown in the optical image I62 in a visually identifiable manner.

The mark 72 indicating the tissue piercing point is superposed on the optical image I62. The location of the tissue piercing point in the optical image I62 is calculated by the processing circuitry 41 based on a result of positioning between the optical image and the medicament administration plan image. As the mark 72, an arrow indicating the tissue piercing point may be used, for example. In the medicament administration plan image I63, a mark 631 indicating an endoscope position and a mark 632 indicating a targeted position are shown. In step SD3, the ultrasonic endoscope 5 is located near the targeted position; thus, the mark 631 and the mark 632 are close to each other.

Since ultrasonic imaging has not yet been performed by the ultrasonic endoscope 5 even by the time of performing step SD3, no ultrasonic image is displayed in the display section I60. Ultrasonic imaging may be performed by the ultrasonic endoscope 5 at the time of step SD3, and in this case, an ultrasonic image generated by the ultrasonic imaging may be displayed in the display section I60.

The display section I64 displays a support message that supports advancing of the ultrasonic endoscope 5 to the targeted position in accordance with a difference in distance between the endoscope current position and the endoscope-targeting arrival point. For example, if the difference in distance is larger than a threshold (hereinafter a "second threshold"), the processing circuitry 41 displays a support message, for example "Reached the vicinity of the targeted position. The puncture needle will pierce at the tissue piercing point. Advance the endoscope a little further". The second threshold is a threshold for distinguishing a status where the endoscope current position is sufficiently close to the endoscope-targeting arrival point from a status where the endoscope current position is not close to the endoscope-targeting arrival point, and is set at a value smaller than the first threshold.

After step SD3, the processing circuitry 41 determines whether or not the endoscope current position has already reached the endoscope-targeting arrival point (step SD4). Specifically, in step SD4, the processing circuitry 41 determines whether or not the difference in distance is larger than the second threshold. If the difference in distance is larger than the second threshold (No in step SD4), the processing circuitry 41 proceeds to step SD3, and superposes a mark indicating the tissue piercing point on the optical image in the guidance window. A technician, etc. looks at the optical image I62, the medicament administration plan image I63, and the support message as shown in FIG. 17 so as to be aware of the endoscope current position and the endoscope-targeting arrival point, so that he or she can advance the ultrasonic endoscope 5 to the endoscope-targeting arrival point. For example, through checking the mark 72 superposed on the optical image I62 and the marks 631 and 632 added to the medicament administration plan image I63, the technician, etc. can carefully advance the ultrasonic endoscope 5 toward the position indicated by the mark 72 superposed on the optical image I62.

If the difference in distance is smaller than the second threshold (Yes in step SD4), the processing circuitry 41, through the realization of the display controlling function 414, displays the tumor piercing point and the medicament injection point in the ultrasonic image (step SD5). In step SD5, the processing circuitry 41 superposes the mark indicating the tumor piercing point and the mark indicating the medicament injection point on the ultrasonic image displayed on the guidance window. For example, if the difference in distance is smaller than the second threshold, the processing circuitry 41 transmits an instruction to perform ultrasonic imaging to the ultrasonic endoscope 5, and upon receipt of the instruction, the ultrasonic endoscope 5 performs ultrasonic imaging using the ultrasonic imaging apparatus provided at the distal end of the insertion unit and generates an ultrasonic image relating to the inside of the patient's body. The generated ultrasonic image is supplied to the medicament administration guiding apparatus 4. The ultrasonic image is displayed on the display device 45 in a real-time manner. The mark indicating a tumor piercing point is an example of guidance information.

Figure 18:
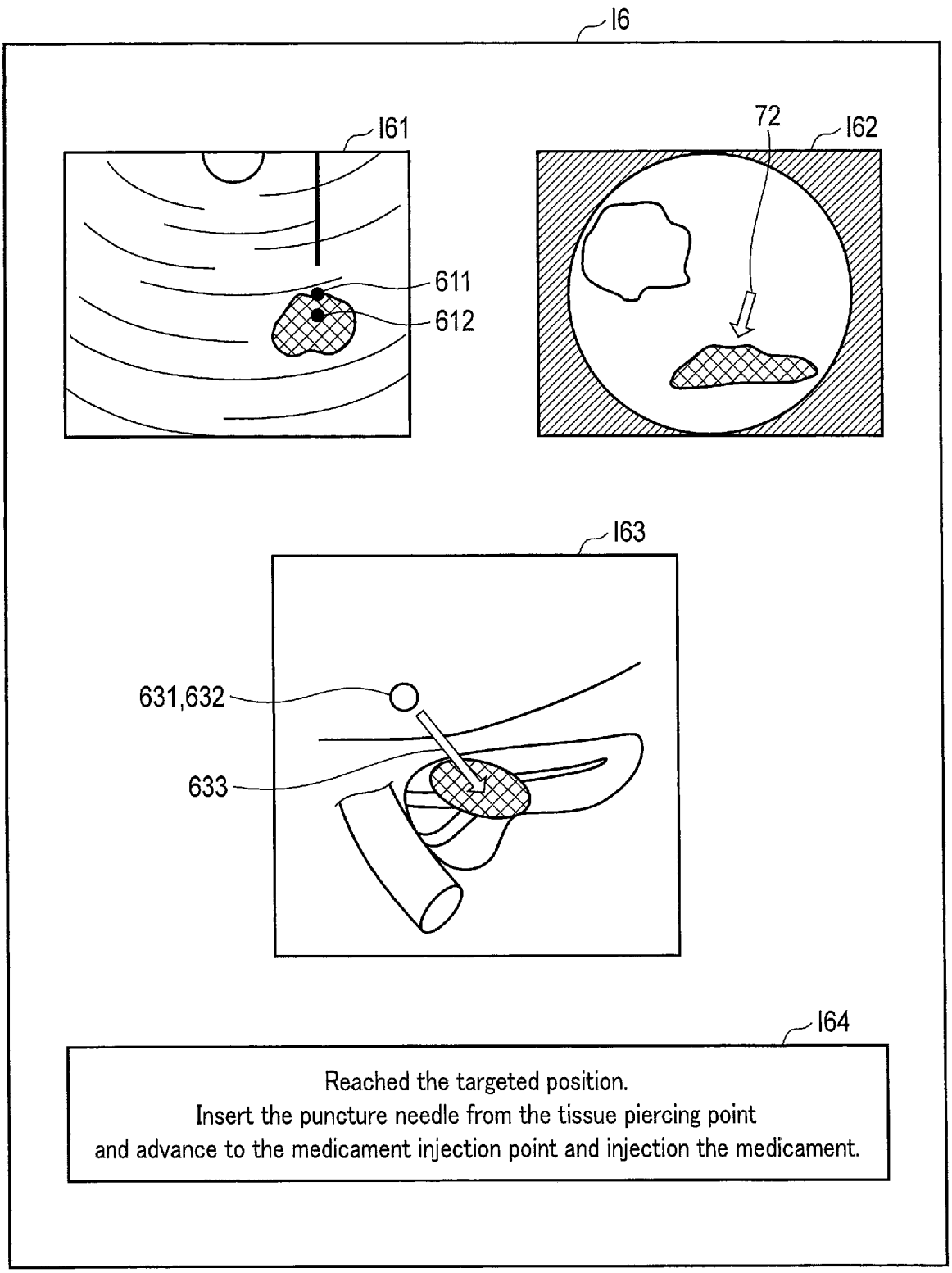
FIG. 18 is a diagram showing an example of a guide window displayed in step SD5.

FIG. 18 is a diagram showing an example of the guide window I6 displayed in step SD5. As shown in FIG. 18, the guide screen I6 displays the ultrasonic image I61 generated by the ultrasonic endoscope 5 in a real-time manner. On the ultrasonic image I61, the mark 611 indicating the tumor piercing point and the mark 612 indicating the medicament injection point are superposed. The positions of the tumor piercing point and the medicament injection point are calculated by the processing circuitry 41 based on the positioning between the ultrasonic image and the medicament administration plan image. On the optical image I62, the mark 72 indicating the tissue piercing point is superposed in the same manner as step SD3.

In the medicament administration plan image I63, the mark 631 indicating the endoscope position and the mark 632 indicating the targeted point are displayed. Since the ultrasonic endoscope 5 is located at the targeted position in step SD5, the mark 631 and the mark 632 are superposed. If the difference in distance is smaller than the second threshold, the processing circuitry 41 superposes the mark 633 indicating a path from the targeted position to the medicament injection point on the medicament administration plan image I63. It is thereby possible to visually check the insertion direction of the puncture needle, etc.

The display section I64 displays a support message that supports advancing of the ultrasonic endoscope 5 to the targeted position in accordance with a difference in distance between the position and the endoscope-targeting arrival point. For example, if the difference in distance is smaller than the second threshold, the processing circuitry 41 displays a support message, for example "Reached the targeted position. Insert the puncture needle from the tissue piercing point and advance to the medicament injection point and inject the medicament." It is thereby possible for a technician, etc. to confirm that the ultrasonic endoscope 5 has reached the targeted position and that the puncture needle should be inserted to inject a medicament, for example.

In step SD5, if the difference in distance is smaller than the second threshold, the processing circuitry 41 may display the medicament injection amount, the medicament injection speed, and the injection timing on the guidance window I6.

Thus, the medicament administration guiding process is finished.

As shown in FIG. 15, the processing circuitry 41, through the realization of the display controlling function 414, changes the guidance information for guiding the ultrasonic endoscope 5 to the targeted position in accordance with the difference in distance between the endoscope current position and the endoscope-targeting arrival point. For example, if the difference in distance is larger than the first threshold, the processing circuitry 41 adds the invasion direction of the ultrasonic endoscope 5 to the optical image as the guidance information. If the difference in distance is smaller than a threshold, the processing circuitry 41 adds the tissue piercing point to the optical image as the guidance information. The processing circuitry 41 displays a support message categorized in accordance with the difference in distance, as shown in FIGS. 16 to 18. The processing circuitry 41 switches between display and non-display of the ultrasonic image in accordance with the difference in distance, as shown in FIGS. 16 to 18. For example, if the difference in distance is larger than the second threshold, the processing circuitry 41 does not supply an instruction to perform imaging to the ultrasonic imaging apparatus and turns off the display of the ultrasonic image; on the other hand, if the difference in distance is smaller than the second threshold, the processing circuitry 41 supplies an instruction to perform imaging to the ultrasonic imaging apparatus and turns on the display of the ultrasonic image. If the difference in distance is smaller than the second threshold, the processing circuitry 41 adds the medicament injection point to the ultrasonic image.

The medicament administration guidance processing can be modified in various ways. For example, in the foregoing embodiment, the processing circuitry 41 is configured to constantly display an optical image when a medicament administration guiding process is performed. However, the embodiment is not limited to this, and the processing circuitry 41 may be configured to constantly display an ultrasonic image instead of an optical image. The processing circuitry 41 does not need to display both an optical image and an ultrasonic image. In this case, the processing circuitry 41 displays a medicament administration plan image and adds an ultrasonic endoscope current position and an ultrasonic endoscope-targeting arrival point to the medicament administration plan image so as to support a technician, etc.

The ultrasonic endoscope 5 was described as an example of a medicament injection device; however, the embodiment is not limited to this example. For example, as the medicament injection device, an endoscope that has no optical imaging apparatus but has an ultrasonic imaging apparatus, or an endoscope that has no ultrasonic imaging apparatus but has an optical imaging apparatus may be provided. In the case of the former endoscope, an ultrasonic image is displayed on a guide window during the medicament administration guiding process; in the case of the latter endoscope, an optical image is displayed.

In some of the foregoing embodiment examples, the processing circuitry 31 simulates the flow of a medicament and generates a medicament distribution based on a medical image and medicament administration parameters of a medicament administration plan. However, the present embodiment is not limited thereto. The processing circuitry 31, through the realization of the medicament distribution generating function 313, generates a medicament distribution using a machine learning model. As a machine learning model, a neural network is used, for example.

FIG. 19 is a diagram showing an input/output relationship of a machine learning model that generates a medicament distribution. As shown in FIG. 19, learning parameters are trained so that the machine learning model outputs a medicament distribution upon input of medicament administration parameters and a medical image. The learning parameters are parameters trained by machine learning, such as weight coefficients or bias, etc. of the machine learning model. For example, the machine learning model is generated based on an input learning sample, which is a combination of medicament administration parameters and a medical image, and an output learning sample, which is a medicament distribution. The medicament distribution as the output learning sample is, as described above, preferably generated through simulation of the flow of a medicament based on medical administration parameters and a medical image, which constitutes the input learning sample. Through using the machine learning model, a medicament distribution can be easily obtained.

In the foregoing embodiment examples, the descriptions did not refer to how many hours elapsed after the start of the medicament injection the generated medicament distribution represents. The processing circuitry 31 may generate a medicament distribution that represents distribution after designated number of hours has elapsed after the start of medicament injection, based on the above-described medicament flow simulation. It suffices that the designated numbers is designated by a user via the input interface 37.

The processing circuitry 31 generates time series of changes in the medicament distribution and determines timing for radiation irradiation in accordance with the time series of changes. For example, the processing circuitry 31 may generate a plurality of medicament distributions respectively corresponding to different lengths of time elapsed since the medicament injection started, specify a most preferable medicament distribution from the generated medicament distributions, and determine a length of elapsed time corresponding to the specified medicament distribution as timing for radiation irradiation. A plurality of medicament distributions respectively corresponding to different lengths of elapsed times are examples of the time series of changes of the medicament distribution. The processing circuitry 31 may calculate the time series of changes of the administered medicament amount in a tumor area or a particular area, such as a risk organ, as the time series of changes of the medicament distribution. The processing circuitry 31 can determine radiation irradiation timing in accordance with radiotherapy strategies, etc. For example, a length of elapsed time at which the administered medicament amount in a tumor area becomes maximum may be determined as radiation irradiation timing. As another example, a length of elapsed time at which the administered medicament amount in a risk organ area becomes maximum may be determined as radiation irradiation timing. As yet another example, a user may designate radiation irradiation timing.

FIG. 20 is a diagram showing an example of the designation window I8 for radiation timing. The designation window I8 is displayed on the display device 35. As shown in FIG. 20, three medicament distributions I812, I822, and I832 respectively corresponding to three different elapsed times are displayed in the designation window I8. The medicament distributions I812, I822, and I832 are displayed with respectively corresponding labels I811, I821, and I823, each indicating a length of elapsed time. For example, the medicament distribution I812 of after "6 hours" elapsed since the medicament injection started, the medicament distribution I822 after "12 hours" elapsed since the medicament injection started, and the medicament distribution I832 after "24 hours" elapsed since the medicament injection started are displayed side by side. The side-by-side display of the medicament distributions I812, I822, and I832 allows a user to visually understand the differences between the medicament distributions depending on the differences in elapsed time. A medicament administration plan, etc. may be displayed in addition to the medicament distributions. Furthermore, a superposed image in which the medicament distributions I812, I822, and I832 are superposed on a radiation dose image.

As shown in FIG. 20, the designation screen I8 displays designation buttons I813, I823, and I833 for designating the radiation irradiation timing are displayed side by side, with respectively corresponding medicament distributions I812, I822, and I832. When one of the designation buttons I813, I823, and I833 is pressed by a user via the input interface 37, the designated elapsed timing corresponding to the medicament distribution is determined as radiation irradiation timing. Thus, appropriate radiation irradiation timing at which potentiation between the medicament and radiation is most significantly exhibited can be determined. The medicament distribution corresponding to the designated radiation irradiation timing is used as a medicament distribution in the above-described medication-combined radiotherapy plan.

A display format for the time series of changes in the medicament distribution is not limited to the display shown in FIG. 20, where multiple medicament distributions respectively corresponding to multiple elapsed times are displayed in parallel. For example, a medicament distribution corresponding to a single elapsed time designated by a slider bar, etc., may be displayed. It is possible to discretionarily change the elapsed time of the display target via the slider bar.

According to at least one of the foregoing embodiments, medicament administration to a tumor can be supported.

The term "processor" used in the above explanation indicates, for example, a circuit, such as a CPU, a GPU, or an Application Specific Integrated Circuit (ASIC), and a programmable logic device (for example, a Simple Programmable Logic Device (SPUD), a Complex Programmable Logic Device (CPLD), and a Field Programmable Gate Array (FPGA)). The processor realizes its function by reading and executing the program stored in the storage circuitry. The program may be directly incorporated into the circuit of the processor instead of being stored in the storage circuit. In this case, the processor implements the function by reading and executing the program incorporated into the circuit. The function corresponding to the program may be realized by a combination of logic circuits, not by executing the program. Each processor of the present embodiment is not limited to a case where each processor is configured as a single circuit; a plurality of independent circuits may be combined into one processor to realize the function of the processor. Further, a plurality of components shown in FIG. 1, FIG. 4 and FIG. 12 may be integrated into one processor to achieve their functions.

While certain embodiments have been described, these embodiments have been presented by way of example only, and are not intended to limit the scope of the inventions. Indeed, the embodiments described herein may be embodied in a variety of other forms; furthermore, various omissions, substitutions, changes, and combinations of embodiments in the form of the embodiment described herein may be made without departing from the spirit of the invention. The accompanying claims and their equivalents are intended to cover such forms or modifications as would fall within the scope and spirit of the invention.

Regarding the foregoing embodiments, the appendage of the following is disclosed as one aspect and selective features of the invention.

(Additional Note 1)

A radiotherapy support system comprising a processing circuitry, the circuit being configured to:
  obtain a distribution of a medicament administered to a tumor;
  obtain a distribution of a dose of radiation applied to the tumor; and
  produce a radiotherapy plan for the tumor using a combination of the medicament and the radiation based on the medicament distribution and the dose distribution.

(Additional Note 2)

The processing circuitry may change at least one of the medicament distribution or the dose distribution for an area where the medicament distribution overlaps the dose distribution, and produce the radiotherapy plan based on the changed distribution.

(Additional Note 3)

The processing circuitry may change the dose distribution based on the medicament distribution and produce the radiotherapy plan based on the changed medicament distribution and the changed dose distribution.

(Additional Note 4)

The processing circuitry may change the medicament distribution based on the dose distribution and produce the radiotherapy plan based on the changed medicament distribution and the changed dose distribution.

(Additional Note 5)

The processing circuitry may output information by which whether or not distribution of at least one of the medicament or the dose exceeds an allowable value can be identified.

(Additional Note 6)

The processing circuitry may superpose the dose distribution and the medicament distribution and display them together with the identifiable information.

(Additional Note 7)

The processing circuitry may superpose the dose distribution and the medicament distribution and display them together with the identifiable information.

(Additional Note 8)

The processing circuitry may produce a medicament administration plan including administration conditions for a medicament administered to the tumor and produce the medicament distribution based on the medicament administration plan.

(Additional Note 9)

The medicament administration conditions may include a position of the tumor and a targeted position of a medicament injection device for the medicament administered to the tumor.

(Additional Note 10)

The medicament injection device may include an endoscope to which a needle for injecting the medicament is attached,
  the processing circuitry may determine a first piercing point and a second piercing point as the targeted position,
  the first piercing point may be a location at which the needle is first inserted into the anatomical tissue,
  the second piercing point may be a location at which the needle is inserted into the tumor which is located deeper than the anatomical tissue.

(Additional Note 11)

The medicament injection device may include an endoscope to which a needle for injecting the medicament is attached,
  the processing circuitry may determine a piercing point and a device arrival point as the targeted position,
  the piercing point may be a position at which the needle is first inserted into the anatomical tissue and/or a position at which the needle is inserted into the tumor which is located deeper than the anatomical tissue,
  the device arrival point may be a position at which the needle can be inserted from the piercing point and may be a position of the endoscope within luminal tissue of the patient.

(Additional Note 12)

The medicament administration conditions may include an injection point and an injection amount of the medicament, and
  the processing circuitry may calculate the medicament distribution based on forms and properties of at least one of the tumor or peripheral anatomical tissue, the injection point, and the injection amount of the medicament.

(Additional Note 13)

The processing circuitry may output guidance information that guides the medicament injection device to an administration position based on the medicament distribution.

(Additional Note 14)

The processing circuitry may further comprise an imaging apparatus provided in a medicament injection device that administers the medicament, the imaging apparatus generating an ultrasonic image and/or an optical image of the inside of luminal tissue of the patient, and
  the processing circuitry may superpose guidance information for guiding the medicament injection device to the targeted position of the medicament injection device, on the ultrasonic image and/or optical image.

(Additional Note 15)

The processing circuitry may detect a current position of the medicament injection device, and may change the guidance information in accordance with a distance between the current position and the targeted position.

(Additional Note 16)

The processing circuitry may display the medical image to which the current position is added and the ultrasonic image and/or the optical image, side by side.

(Additional Note 17)

The processing circuitry may set conditions for a radiation dose administered to the tumor, and may produce the dose distribution based on the radiation administration conditions.

(Additional Note 18)

The processing circuitry may generate time series of changes of the medicament distribution and determine timing for irradiation of the radiation in accordance with the time series of changes.

(Additional Note 19)

The processing circuitry may produce multiple radiotherapy plans differing from each other, based on the medicament distribution and the dose distribution, and may display a list of the multiple generated radiotherapy plans.

(Additional Note 20)

A radiotherapy support method comprising:
  obtaining a distribution of a medicament administered to a tumor;
  obtaining a distribution of a dose of radiation administered to the tumor; and
  producing a radiotherapy plan for the tumor using a combination of the medicament and the radiation based on the medicament distribution and the dose distribution;

(Additional Note 21)

A radiotherapy support system comprising a processing circuitry configured to:
  obtain a medical image relating to a patient; and
  produce a medicament administration plan including a location of a tumor and a target site for a medicament injection device that injects a medicament administered to the tumor, in accordance with forms and properties of the tumor and anatomical tissue shown in the medical image.

(Additional Note 22)

The processing circuitry may determine an injection amount and an injection speed of the medicament in addition to the targeted position, as the medicament administration plan.

(Additional Note 23)

The medicament injection device includes an endoscope to which a needle for injecting the medicament is attached,
the processing circuitry determines a first piercing point and a second piercing point as the targeted position,
the first piercing point may be a location at which the needle is first inserted into the anatomical tissue,
the second piercing point may be a location at which the needle is inserted into a tumor which is located deeper than the anatomical tissue.

(Additional Note 24)

The medicament injection device includes an endoscope to which a needle for injecting the medicament is attached,
the processing circuitry determines a piercing point and a device arrival point as the targeted position,
the piercing point is a position at which the needle is first inserted into the anatomical tissue and/or a position at which the needle is inserted into the tumor which is located deeper than the anatomical tissue,
the device arrival point may be a position at which the needle can be inserted from the piercing point and may be a position of the endoscope within luminal tissue of the patient.

(Additional Note 25)

The processing circuitry may display the medical image to which the targeted position is added.

(Additional Note 26)

The processing circuitry may generate a medicament distribution that represents a predicted spatial distribution of an administered medicament amount relating to the tumor, based on forms and properties of at least one of the tumor or peripheral anatomical tissue, the injection point and the injection amount of the medicament.

(Additional Note 27)

The processing circuitry may display the medicament distribution.

(Additional Note 28)

The processing circuitry may generate a dose distribution that represents a predicted spatial distribution of a dose administered to the tumor, and may display a superposition of the medicament distribution and the dose distribution.

(Additional Note 29)

The processing circuitry may increase or reduce the administered dose allocated to each pixel of the dose distribution relating to the patient, based on the administered medicament amount allocated to each pixel of the medicament distribution.

(Additional Note 30)

The processing circuitry may increase or decrease the administered medicament amount allocated to each pixel of the dose distribution, based on the administered dose allocated to each pixel of the dose distribution.

(Additional Note 31)

The processing circuitry may generate a plurality of dispersion distributions, changing the injection point and the injection amount of the medicament by the medicament injection device, and may determine, as the medicament administration plan, a specific injection point and a specific injection amount corresponding to a specific dispersion distribution of the plurality of dispersion distributions.

(Additional Note 32)

The processing circuitry may determine, as a medicament administration plan, an injection amount of medicament based on body measurement information of the patient and measurement information of biological matter.

(Additional Note 33)

The processing circuitry may determine, based on the tumor location, whether an injection syringe having a needle for injecting a medicament from the skin surface or the endoscope having a puncture needle for injecting a medicament within the body should be used as a medicament injection device.

(Additional Note 34)

The processing circuitry may search for a specific blood vessel that connects to the tumor, and if the specific blood vessel is specified, may produce the medicament administration plan for injecting the medicament into the specific blood vessel.

(Additional Note 35)

The processing circuitry may comprise an imaging apparatus provided in the medicament injection device generating an ultrasonic image and/or an optical image of the inside of luminal tissue of the patient, and The processing circuitry may superpose guidance information for guiding the medicament injection device to the targeted position of the medicament injection device, on the ultrasonic image and/or optical image.

(Additional Note 36)

The processing circuitry may detect a current position of the medicament injection device, and may change the guidance information in accordance with a distance between the current position and the targeted position.

(Additional Note 37)

The medicament injection device is an ultrasonic endoscope having a puncture needle, and
the processing circuitry may add, if the distance is larger than a threshold, an invasion direction of the ultrasonic endoscope to the optical image as the guidance information, and may add, if the distance is smaller than the threshold, a position at which the puncture needle pierces to the optical image as the guidance information.

(Additional Note 38)

The processing circuitry may add, if the distance is smaller than a threshold, a position at which a medicament is injected from the puncture needle to the ultrasonic image as the guidance information.

(Additional Note 39)

The processing circuitry may display the medical image to which the current position is added and the ultrasonic image and/or the optical image, side by side.

(Additional Note 40)

A computer may obtain a medical image relating to a patient, and
the computer may produce a medicament administration plan that includes the tumor location and a targeted position for the medicament injection device that injects a medicament administered to the tumor, based on forms and properties of the tumor and analogical tissue shown in the medical image.

The invention claimed is:

1. A radiotherapy support system, comprising:
processing circuitry being configured to
obtain a medicament distribution of a medicament to be administered to a tumor;

obtain a distribution of a dose of radiation to be applied to the tumor; and produce a radiotherapy plan for the tumor using a combination of the medicament and the radiation, based on the obtained medicament distribution and the obtained dose distribution, wherein the processing circuitry is further configured to produce a medicament administration plan including medicament administration conditions for the medicament to be administered to the tumor, and produce the medicament distribution based on the produced medicament administration plan, the medicament administration conditions include an injection point and an injection amount of the medicament, the processing circuitry is further configured to calculate the medicament distribution based on forms and properties of at least one of the tumor or peripheral anatomical tissue, the injection point, and the injection amount of the medicament, and output, during use of a medicament injection device, which includes a needle for injecting the medicament, by an operator, guidance information that guides the operator to move the medicament injection device to an administration position, based on the calculated medicament distribution, wherein the radiotherapy support system further comprises an imaging apparatus provided in the medicament injection device that administers the medicament, the imaging apparatus generating an ultrasonic image or an optical image of an inside of luminal tissue of a patient, and a display device that superimposes guidance information to guide the medicament injection device to a targeted position of the medicament injection device, on the ultrasonic image or the optical image, the processing circuitry is further configured to determine a first piercing point and a second piercing point as the targeted position based on a positional relationship between the tumor included in the ultrasonic image and/or the optical image and the peripheral anatomical tissue in which the tumor is present, which differs from the luminal tissue, the first piercing point is a first location at which the needle is first inserted into the luminal tissue, the second piercing point is a second location at which the needle is inserted into the tumor, which is located deeper than the luminal tissue, the display device superimposes a first mark indicating the administration position and a second mark indicating the targeted position of the medicament injection device on the ultrasonic image or the optical image, and the display device displays a medical image to which a current position of the medicament injection device is added, the ultrasonic image, and the optical image, side by side.

2. The radiotherapy system according to claim 1, wherein the processing circuitry is further configured to change at least one of the medicament distribution or the dose distribution for an area where the medicament distribution overlaps the dose distribution, and produce the radiotherapy plan based on the changed distribution.

3. The radiotherapy support system according to claim 2, wherein the processing circuitry is further configured to change the dose distribution based on the medicament distribution, and produce the radiotherapy plan based on the changed medicament distribution and the changed dose distribution.

4. The radiotherapy support system according to claim 2, wherein the processing circuitry is further configured to change the medicament distribution based on the dose distribution, and produce the therapy plan based on the changed medicament distribution and the changed dose distribution.

5. The radiotherapy support system according to claim 2, wherein the processing circuitry is further configured to output information to determine whether or not distribution of at least one of the medicament or the dose exceeds an allowable value.

6. The radiotherapy support system according to claim 5, wherein the processing circuitry is further configured to superimpose and display the dose distribution and the medicament distribution together with identifiable information.

7. The radiotherapy support system according to claim 5, wherein the processing circuitry is further configured to display the dose distribution and the medicament distribution side by side, together with identifiable information.

8. The radiotherapy support system according to claim 1, wherein the medicament administration conditions include a position of the tumor and the targeted position of the medicament injection device configured to inject the medicament administered to the tumor.

9. The radiotherapy support system according to claim 1, wherein
the medicament injection device includes an endoscope with the needle attached to inject the medicament,
the processing circuitry is further configured to determine a device arrival point, and
the device arrival point is a position where the needle can be inserted from the first piercing point and is a position of the endoscope within the luminal tissue of the patient.

10. The radiotherapy support system according to claim 1, wherein
the processing circuitry is further configured to detect the current position of the medicament injection device, and
the display device changes the guidance information in accordance with a distance between the current position and the targeted position.

11. The radiotherapy support system according to claim 1, wherein the processing circuitry is further configured to:
set conditions for a radiation dose administered to the tumor; and
produce the dose distribution based on the radiation administration conditions.

12. The radiotherapy support system according to claim 1, wherein the processing circuitry is further configured to
produce multiple radiotherapy plans differing from each other, based on the medicament distribution and the dose distribution, and
display a list of the multiple generated radiotherapy plans.

13. The radiotherapy support system according to claim 1, wherein the processing circuitry is further configured to generate a time series of changes of the medicament distribution and determine a timing for irradiation of the radiation in accordance with the time series of changes.

14. A radiotherapy support method, comprising:
obtaining a distribution of a medicament administered to a tumor;
obtaining a distribution of a dose of radiation applied to the tumor; and producing a radiotherapy plan for the tumor using a combination of the medicament and the radiation based on the obtained medicament distribution and the obtained dose distribution, wherein the method further comprises producing a medicament administration plan including medicament administration conditions for the medicament to be administered to the tumor, and producing the medicament distribution based on the produced medicament administration plan, wherein the medicament administration conditions include an injection point and an injection amount of the medicament, calculating the medicament distribution based on forms and properties of at least one of the tumor or peripheral anatomical tissue, the injection point, and the injection amount of the medicament, outputting, during use of a medicament injection device, which includes a needle for injecting the medicament, by an operator, guidance information that guides the operator to move the medicament injection device to an administration position, based on the obtained medicament distribution, generating, by an imaging apparatus provided in the medicament injection device that administers the medicament, an ultrasonic image or an optical image of an inside of luminal tissue of a patient; and superimposing, by a display device, guidance information to guide the medicament injection device to a targeted position of the medicament injection device, on the ultrasonic image or the optical image, wherein the display device superimposes a first mark indicating the administration position and a second mark indicating the targeted position of the medicament injection device on the ultrasonic image or the optical image, wherein the method further comprises:

determining a first piercing point and a second piercing point as the targeted position based on a positional relationship between the tumor included in the ultrasonic image and/or the optical image and the peripheral anatomical tissue in which the tumor is present, which differs from the luminal tissue, the first piercing point is a first location at which the needle is first inserted into the luminal tissue, and the second piercing point is a second location at which the needle is inserted into the tumor, which is located deeper than the luminal tissue; and displaying, by the display device, a medical image to which a current position of the medicament injection device is added, the ultrasonic image, and the optical image, side by side.

\* \* \* \* \*